(12) United States Patent
Mitsui

(10) Patent No.: US 9,404,850 B2
(45) Date of Patent: Aug. 2, 2016

(54) MICROSCOPE SYSTEM, IMAGE PROCESSING APPARATUS, AND COMPUTER READABLE RECORDING MEDIUM

(71) Applicant: OLYMPUS CORPORATION, Tokyo (JP)

(72) Inventor: Masanori Mitsui, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 534 days.

(21) Appl. No.: 13/908,391

(22) Filed: Jun. 3, 2013

(65) Prior Publication Data

US 2013/0265406 A1  Oct. 10, 2013

Related U.S. Application Data

(63) Continuation of application No. PCT/JP2012/050542, filed on Jan. 13, 2012.

(30) Foreign Application Priority Data

Jan. 21, 2011  (JP) .................................. 2011-011025

(51) Int. Cl.
*H04N 7/18* (2006.01)
*G01N 21/25* (2006.01)
*G02B 21/36* (2006.01)
*G01J 3/02* (2006.01)
*G02B 21/26* (2006.01)

(52) U.S. Cl.
CPC .............. *G01N 21/255* (2013.01); *G01J 3/027* (2013.01); *G01J 3/0248* (2013.01); *G01J 3/0291* (2013.01); *G01N 21/251* (2013.01); *G02B 21/365* (2013.01); *G02B 21/26* (2013.01)

(58) Field of Classification Search
CPC .  G01N 21/255; G01N 21/251; G02B 21/365; G02B 21/26; G01J 3/0291; G01J 3/0248; G01J 3/027
See application file for complete search history.

(56) References Cited

U.S. PATENT DOCUMENTS

| | | | | |
|---|---|---|---|---|
| 5,631,166 A | * | 5/1997 | Jewell .................... | G01N 21/07 422/537 |
| 2004/0046946 A1 | * | 3/2004 | Kim ...................... | H04N 9/3117 353/101 |
| 2006/0252988 A1 | * | 11/2006 | Ayame ............... | A61B 1/00009 600/109 |
| 2009/0010922 A1 | * | 1/2009 | Sabbadini .............. | C07K 16/44 424/130.1 |
| 2009/0069674 A1 | * | 3/2009 | Masumura ........... | A61B 5/0073 600/425 |
| 2009/0274351 A1 | * | 11/2009 | Otsuka ................. | G06K 9/4652 382/128 |
| 2010/0083410 A1 | * | 4/2010 | Hattori ............... | G02B 21/0032 850/1 |
| 2010/0128263 A1 | * | 5/2010 | Kobayashi ................ | G01J 3/06 356/300 |

* cited by examiner

*Primary Examiner* — Tat Chio
(74) *Attorney, Agent, or Firm* — Scully, Scott, Murphy & Presser, P.C.

(57) ABSTRACT

A microscope system includes: a microscope that generates an observation image of a specimen; an image obtaining unit that obtains an RGB image of the specimen; a spectroscopic information obtaining unit that obtains spectroscopic information of the specimen; an analyzer that analyzes the RGB image; a determining unit that determines a necessity of obtaining the spectroscopic information based on a result of the analysis of the analyzer; and a control unit that controls an operation of the spectroscopic information obtaining unit based on a result of the determination of the determining unit.

14 Claims, 16 Drawing Sheets

| NUCLEUS AREA | AREA | PERIMETER | DEGREE OF CIRCULARITY |
|---|---|---|---|
| a1 | 8.0 | 11.0 | 0.83 |
| a2 | 3.1 | 7.9 | 0.62 |
| a3 | 3.2 | 8.6 | 0.54 |
| a4 | 4.7 | 9.2 | 0.69 |
| a5 | 4.9 | 10.3 | 0.58 |
| ... | ... | ... | ... |

MICROSCOPE SYSTEM, IMAGE PROCESSING APPARATUS, AND COMPUTER READABLE RECORDING MEDIUM

CROSS-REFERENCE TO RELATED APPLICATIONS

This application is a continuation of International Application No. PCT/JP2012/050542, designating the United States and filed on Jan. 13, 2012 which claims the benefit of priority of the prior Japanese Patent Application No. 2011-011025, filed on Jan. 21, 2011, and the entire contents of the International application and the Japanese Application are incorporated herein by reference.

BACKGROUND OF THE INVENTION

1. Field of the Invention

The present invention relates to a microscope system that processes a pathological specimen image obtained by using a microscope, an information processing apparatus, and a computer readable recording medium.

2. Description of the Related Art

Conventionally, for a diagnosis assistance, a screening, an automatic diagnosis, and the like in a pathological diagnosis, a technique of analyzing an RGB image of a pathological specimen stained with a predetermined dye and detecting an abnormal site and the like to determine a negative/positive status and the like has been known. For example, Japanese Patent Application Laid-Open No. 2009-180539 discloses a technique of analyzing a digital color image and extracting an abnormal area and the like.

A technique of analyzing spectroscopic data of a stained pathological specimen for utilization in diagnosis assistance and the like has been proposed in Japanese Patent Application Laid-Open No. 2003-65948, PCT International Application's Japanese Translation No. 2001-523334, and Japanese Patent Application Laid-Open No. 2008-51654. Japanese Patent Application Laid-Open No. 2003-65948, for example, discloses an image processing method in which a spectral transmittance image is estimated from a signal value of a camera obtained by shooting a tissue specimen, a dye amount distribution of the specimen is calculated from the spectral transmittance image, and a tissue structure and the like are analyzed. Besides, as a method for obtaining spectroscopic data, PCT International Application's Japanese Translation No. 2001-523334, for example, discloses a spectroscopic measurement using a spectrometer and Japanese Patent Application Laid-Open No. 2008-51654 discloses a multiband imaging using an optical filter and an RGB camera.

SUMMARY OF THE INVENTION

According to an aspect of the present invention, a microscope system, includes: a microscope that generates an observation image of a specimen; an image obtaining unit that obtains an RGB image of the specimen; a spectroscopic information obtaining unit that obtains spectroscopic information of the specimen; an analyzer that analyzes the RGB image; a determining unit that determines a necessity of obtaining the spectroscopic information based on a result of the analysis of the analyzer; and a control unit that controls an operation of the spectroscopic information obtaining unit based on a result of the determination of the determining unit.

According to another aspect of the present invention, an information processing apparatus that processes, in a microscope system provided with a microscope that generates an observation image of a specimen, information generated based on an RGB image of the specimen and spectroscopic information, obtained by a spectroscopic information obtaining unit, of the specimen, includes: an analyzer that analyzes the RGB image; a determining unit that determines a necessity of obtaining the spectroscopic information based on a result of the analysis of the analyzer; and a control unit that controls an operation of the spectroscopic information obtaining unit based on a result of the determination of the determining unit.

According to still another aspect of the present invention, in a non-transitory computer readable recording medium with an executable information processing program stored thereon, the program causes, in a microscope system provided with a microscope that generates an observation image of a specimen, information generated based on an RGB image of the specimen and spectroscopic information, obtained by a spectroscopic information obtaining unit, of the specimen to be processed and the program instructs a computer to execute: analyzing the RGB image; determining a necessity of obtaining the spectroscopic information based on a result of the analysis at the analyzing; and controlling an operation of the spectroscopic information obtaining unit based on a result of the determination at the determining.

The above and other features, advantages, and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be explained in detail below with reference to the accompanying drawings. It should be noted that the present invention is not limited to the embodiments. The same part will be assigned with the same reference symbol in the description of the drawings.

First Embodiment

Figure 1:
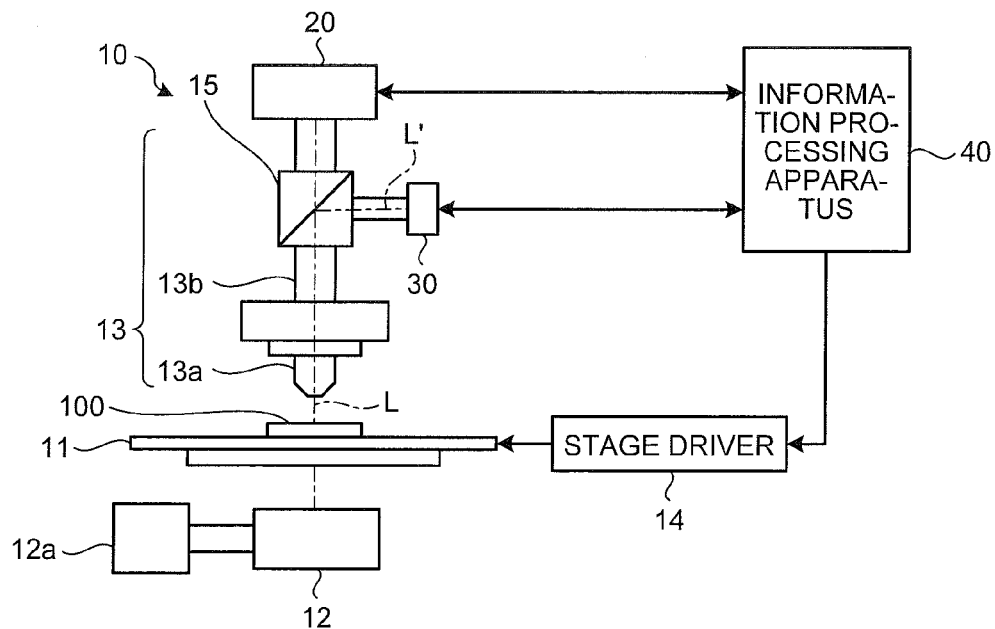
FIG. 1 schematically shows a configuration example of a microscope system according to a first embodiment of the present invention.

FIG. 1 schematically shows a configuration example of a microscope system according to a first embodiment of the present invention. As shown in FIG. 1, a microscope system 1 is provided with a microscope 10 that allows an observation of a specimen 100; an RGB imaging device 20 as an image obtaining unit that obtains an RGB image of the specimen 100; a spectroscopic measurement device 30 as a spectroscopic information obtaining unit that obtains spectroscopic information of the specimen 100; and an information processing apparatus 40 that controls an operation of each unit of the microscope system 1 overall and generates diagnosis information, for example, a presence, a location, feature data of an abnormal site, concerning the specimen 100 based on the information input from the RGB imaging device 20 and the spectroscopic measurement device 30. Each of the RGB imaging device 20 and the spectroscopic measurement device 30 is connected to the information processing apparatus 40 so that data can be transmitted and received.

The microscope 10 is provided with a stage 11 on which the specimen 100 is placed, an illumination optical system 12 that transmits an illumination onto the specimen 100 from a rear surface side, an observation optical system 13 that makes the illumination light transmitted through the specimen 100 incident, and a stage driver 14 that adjusts a position of the stage 11 under a control of the information processing apparatus 40.

The stage 11 is configured in a movable manner along a surface perpendicular to an observation optical axis (optical axis of an objective lens 13a) L and in a direction of the observation optical axis L. This configuration allows an observation target area on the specimen 100 to be adjusted and the specimen 100 to move along the observation optical axis L for focusing, so that the focus is adjusted.

The illumination optical system 12 is configured by arranging a light source 12a that emits an illumination light and various types of optical systems that, not shown, condense the illumination light from the light source 12a and irradiates the specimen 100 at appropriate positions. The illumination light radiated by the illumination optical system 12 on the specimen 100 gets incident on the objective lens 13a as an observation light.

The observation optical system 13 includes the objective lens 13a and a lens barrel 13b arranged above the specimen 100. On an optical path of the lens barrel 13b, a beam splitter 15 that causes an optical path of the observation light transmitted through the objective lens 13a to branch off to the direction of the observation optical axis L and a direction of an optical axis L' perpendicular to the observation optical axis L is provided.

The RGB imaging device 20 is configured by an RGB camera provided with an imaging element such as a CCD. The RGB imaging device 20 captures an observation image of the specimen 100 within a field of view (image obtainment range) which is determined depending on a magnification of the objective lens 13a and generates and outputs to the information processing apparatus 40 image data of an RGB image (RGB image data). An RGB camera is widely used in a digital camera and the like, and an RGB camera of single-plate system in which color filters for R, G, B colors are arranged in the Bayer pattern on a monochrome imaging element or an RGB camera of three-plate system may be used. The RGB imaging device 20 is arranged at an end part of the lens barrel 13b so that a center of an RGB image to be obtained locates on the observation optical axis L.

The spectroscopic measurement device 30 performs a spectroscopic measurement on the observation light of the specimen 100 within an area in a predetermined range (spectroscopic measurement range) and generates and outputs to the information processing apparatus 40 spectroscopic data that represents a light intensity (or an absorbance) for each wavelength band. The spectroscopic measurement device 30 is arranged so that a measurement center (center in the spectroscopic measurement range) locates on the optical axis L'.

Figure 2:
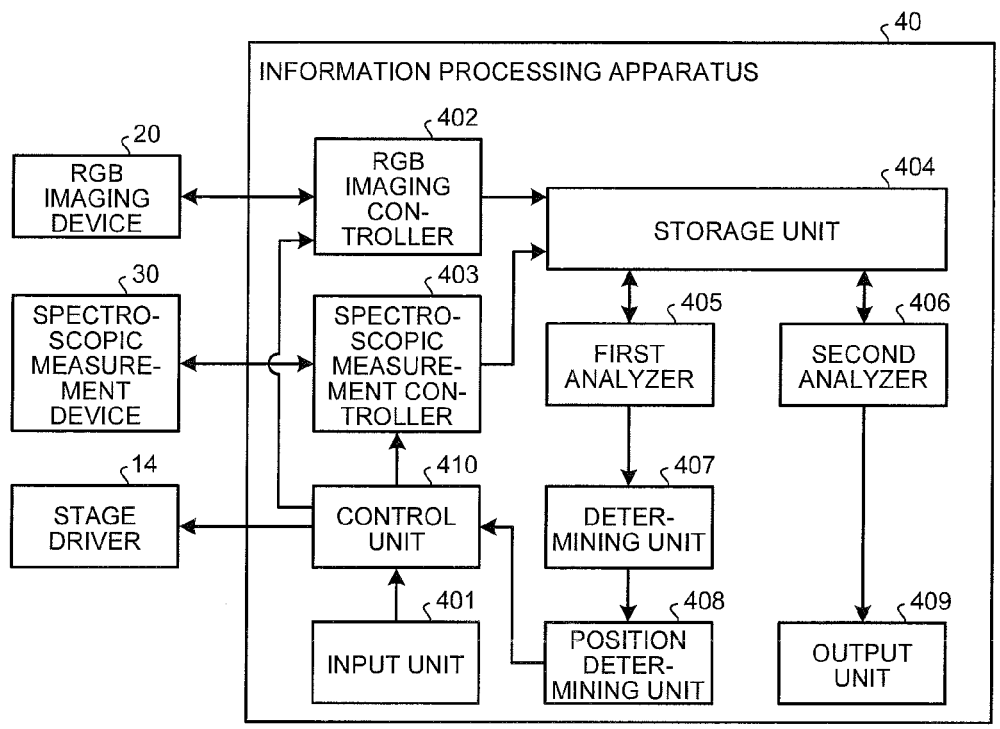
FIG. 2 is a block diagram of a configuration example of the information processing apparatus shown in FIG. 1.

FIG. 2 is a block diagram of a configuration example of the information processing apparatus 40. As shown in FIG. 2, the information processing apparatus 40 is provided with an input unit 401 that accepts an input of information concerning a process in the information processing apparatus 40; an RGB imaging controller 402 that controls an operation of the RGB imaging device 20; a spectroscopic measurement controller 403 that controls an operation of the spectroscopic measurement device 30; a storage unit 404; a first analyzer 405 that analyzes an RGB image obtained in the RGB imaging device 20; a second analyzer 406 that performs an analysis based on image data and spectroscopic data; a determining unit 407 that determines a necessity of obtaining spectroscopic information; a position determining unit 408 that determines a spectroscopic measurement position with respect to the specimen 100; an output unit 409 that outputs information concerning the process in the information processing apparatus 40; and a control unit 410 that controls these units.

The input unit 401 is configured by an input device such as a keyset, a mouse, a touchscreen, and various kinds of switches, for example and outputs to the control unit 410 a signal in accordance with an operational input.

The RGB imaging controller 402 generates and transmits to the RGB imaging device 20 a control signal that causes an execution of an RGB imaging of the specimen 100, accepts an input of RGB image data generated in the RGB imaging device 20, and causes the storage unit 404 to store the image data.

The spectroscopic measurement controller 403 generates and transmits to the spectroscopic measurement device 30 a control signal that causes an execution of the spectroscopic measurement of the specimen 100, accepts an input of spectroscopic data generated in the spectroscopic measurement device 30, and causes the storage unit 404 to store the spectroscopic data.

The storage unit 404 is configured by an IC memory of various kinds such as a ROM and a RAM like a flash memory in which updating storage can be made, a hard disk which is embedded or connected via a data communication terminal, an information recording medium of various kinds (CD-ROM, for example) and a reader for the medium, and the like. The storage unit 404 stores, in addition to the image data and the spectroscopic data of the specimen 100, in advance a program that causes the microscope system 1 to operate and various functions provided in the microscope system 1 to be executed and temporarily stores data to be used in the middle of the program each time when the process is performed.

The first analyzer 405 analyzes an RGB image of the specimen 100, extracts tissues appropriate to an examination purpose from the RGB image, and calculates feature data of each of the extracted tissues.

The second analyzer 406 performs an analysis based on spectroscopic data concerning a spectroscopic measurement position and RGB image data of an area other than the spectroscopic measurement position and generates more detailed analysis information concerning the specimen 100.

The determining unit 407 performs a spectroscopic measurement of the specimen 100 based on a result of the analysis of the first analyzer 405 and determines a necessity of obtaining spectroscopic information (spectroscopic data).

The position determining unit 408 determines, as a spectroscopic measurement position, a position of an abnormal site detected from the RGB image and outputs the positional information.

The control unit 410 gives instructions to and performs data transmission with units constituting the information processing apparatus 40 based on signals input from the input unit 401, the program, the data, and the like stored in the storage unit 404. The control unit 410 controls operations of units constituting the microscope 10 to control an entire operation of the microscope system 1 overall. The control unit 410 controls, for example, the spectroscopic measurement controller 403 and the stage driver 14 to perform a spectroscopic measurement on a spectroscopic measurement position determined by the position determining unit 408.

The output unit 409 is provided with a display device such as an LCD, an EL display, and a CRT display and displays a process status in the information processing apparatus 40, analysis results of the first analyzer 405 and the second analyzer 406, and else information of various kinds under the control of the control unit 410.

The information processing apparatus 40 is configured by a CPU, a main storage device such as a main memory, an external storage device, a communication device, an output device such as a display device, and a known hardware to which each unit of the input unit is connected or which is provided with an interface device and the like connecting an external input. For example, a general-purpose computer such as a workstation and a personal computer can be used as the information processing apparatus 40.

Figure 3:
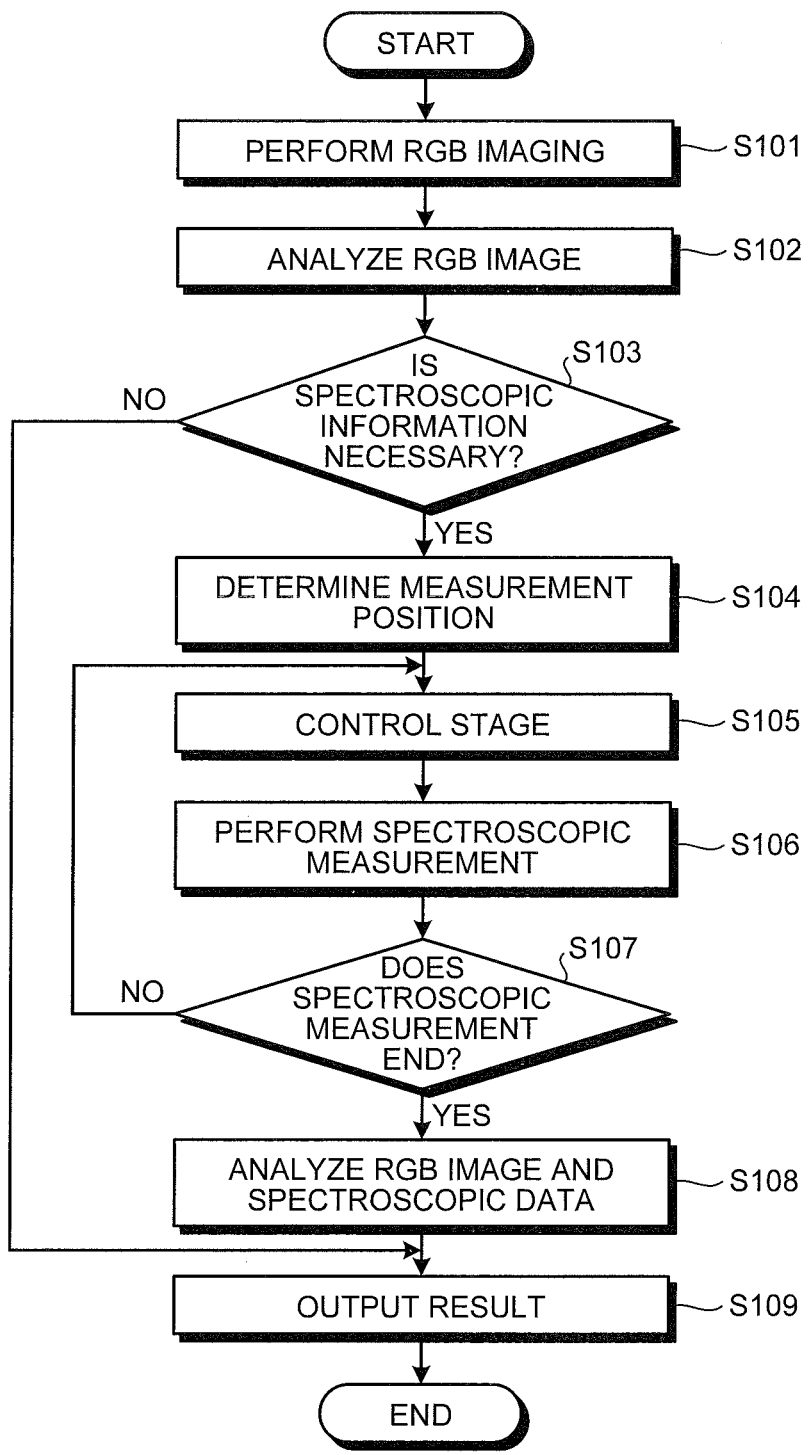
FIG. 3 is a flowchart of an operation of the microscope system shown in FIG. 1.

Next, an operation of the microscope system 1 will be explained. FIG. 3 is a flowchart of an operation of the microscope system 1.

First at step S101, the RGB imaging device 20 performs an RGB imaging with respect to the specimen 100 to obtain an observation image within an image obtainment range. Here, when an examination target is a pathological specimen, the specimen 100 is stained in advance with a predetermined dye (HE staining using two dyes, i.e., hematoxylin and eosin, for example). RGB image data generated by the RGB imaging is stored in the storage unit 404.

At step S102, the first analyzer 405 reads out from the storage unit 404 and analyzes the image data of the RGB image captured at step S101. Specifically, the first analyzer 405 performs tissue classification based on a pixel value of each of pixels constituting the RGB image and calculates feature data of each of extracted tissues. A result of the analysis (feature data of each tissue) is stored in the storage unit 404.

At step S103, the determining unit 407 determines a necessity of obtaining spectroscopic information of the specimen 100 based on the analysis result of the RGB image. Specifically, the determining unit 407 compares, with predetermined values, feature data (a size, i.e., an area; a perimeter; a degree of circularity; an atypism calculated from the perimeter and the degree of circularity, and the like, for example) calculated by the first analyzer 405, and detects a tissue (abnormal site) having feature data larger than a threshold value. The determining unit 407 determines that it is necessary to obtain spectroscopic information when one or more abnormal site is detected in the specimen 100.

Here, tissues having feature data larger than the threshold value include, other than an abnormal tissue (a cancer cell, for example) which is positive in pathology, a normal tissue (negative in pathology) which is detected apparently as an abnormal site due to characteristics of the RGB imaging device 20 and the like. So, the first embodiment is configured to obtain spectroscopic information to obtain more detailed information concerning a tissue extracted as an abnormal site.

When the obtainment of spectroscopic information is determined to be necessary ("Yes" at step S103), the position determining unit 408 determines a position of each of detected abnormal sites as a spectroscopic measurement position (step S104).

At step S105, the control unit 410 controls the stage driver 14 to adjust the position of the stage 11 so that the spectroscopic measurement position determined by the position determining unit 408 is arranged at a center of the measurement by the spectroscopic measurement device 30.

At step S106, the spectroscopic measurement device 30 performs a spectroscopic measurement with respect to each spectroscopic measurement position on the specimen 100 to generate spectroscopic data. More specifically, the control unit 410 controls the spectroscopic measurement controller 403 to perform the spectroscopic measurement at a time when the spectroscopic measurement position almost matches the center of the measurement by the spectroscopic measurement device 30 while adjusting the position of the stage 11. The spectroscopic data thus obtained is stored in the storage unit 404.

At step S107, the control unit 410 determines whether or not the spectroscopic measurement is performed with respect to all positions determined by the position determining unit 408. When there remains a position which needs the spectroscopic measurement ("No" at step S107), the operation returns to step S105.

On the other hand, when the spectroscopic measurement is performed with respect to all the positions ("Yes" at step S107), the second analyzer 406 reads out from the storage unit 404 and analyzes the spectroscopic data and the RGB image data of the specimen 100 (step S108). As an analysis method, various known methods including a method of directly discriminating tissues at each spectroscopic measurement position from the spectroscopic data and extracting and analyzing tissues, a method of calculating predetermined parameters from the spectroscopic data and extracting tissues via the calculated parameters, and the like may be used. In the first embodiment, a method of using a dye amount as a parameter is adopted. Specifically, the second analyzer 406 estimates a dye amount at each spectroscopic measurement position from the spectroscopic data and calculates RGB values for the dye amount. The second analyzer 406 then corrects the RGB image captured at step S101 by using the calculated RGB values. Besides, the second analyzer 406 performs an analysis (extraction of predetermined tissues and calculation of feature data) again with respect to the corrected RGB image.

At step S109, the output unit 409 outputs a result of the analysis on the corrected RGB image. The analysis result to be output includes the corrected RGB image, an image representing tissues extracted from the corrected RGB image, feature data of each of the extracted tissues, and the like. In addition, a result of a follow-up comparison between feature data of each of the extracted tissues with a threshold value and a detected positive abnormal site (a tissue having feature data larger than the threshold value) may be output. Here, the threshold value used on this occasion may be the same as or different from the threshold value used at step S103. For example, a small threshold value may be set to detect as many abnormal sites as possible for RGB image correction at step S103 and a normally-used threshold value may be set to use the analysis result as diagnosis information at step S109.

After that, the operation ends.

When the obtainment of spectroscopic information is determined not to be necessary at step S103 ("No" at step S103), the operation moves directly to step S109. In this case, the output unit 409 outputs the result of the analysis on the RGB image obtained by the first analyzer 405.

As explained above, since insufficient image information in the RGB image of the specimen 100 is corrected by using spectroscopic data, it is possible according to the first embodiment to perform an image analysis with high accuracy. Hence, it becomes possible to realize a diagnosis assistance, a screening, an automatic diagnosis, and the like with high reliability based on the analysis result of the RGB image corrected in this manner.

Besides, since a necessity of performing the spectroscopic measurement with respect to the specimen 100 is determined based on the analysis result on the RGB image and the spectroscopic measurement is performed only with respect to a necessary part (spectroscopic measurement position) on the specimen 100, it becomes possible according to the first embodiment to obtain highly accurate image information (spectroscopic data) without drastically increasing time for measurement. Especially in a case of examining a lot of specimens, it becomes possible to improve examination efficiency and throughput in total since a specimen on which the spectroscopic measurement is performed can be limited.

While the position determining unit 408 automatically determines a spectroscopic measurement position based on the result of the analysis, by the first analyzer 405, on the RGB image in the explanation above, a user may set the spectroscopic measurement position manually. Specifically, a tissue image extracted by the first analyzer 405 is output and displayed in a display device, and a user selects an area on which whether positive or not cannot be determined and performs an input through the input unit 401 while watching the displayed image. It is only necessary that the position determining unit 408 determines the selected area by the input as a spectroscopic measurement position.

EXAMPLE

Next, an example of an image analysis in the microscope system according to the first embodiment will be explained. Here, a case of extracting a nucleus from an HE-stained pathological specimen will be explained.

Figure 4A:
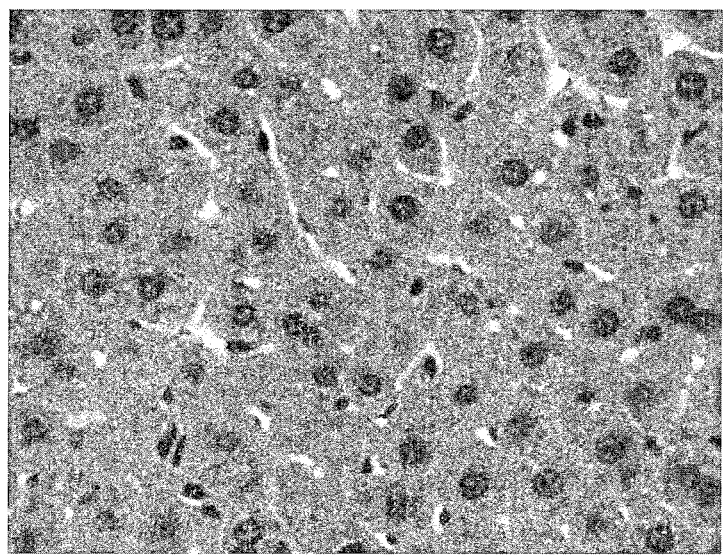
FIG. 4A shows an example of an RGB image of an HE-stained pathological specimen.

FIG. 4A shows an example of an RGB image obtained by performing the RGB imaging at step S101 with respect to an HE-stained pathological specimen.

Figure 4B:
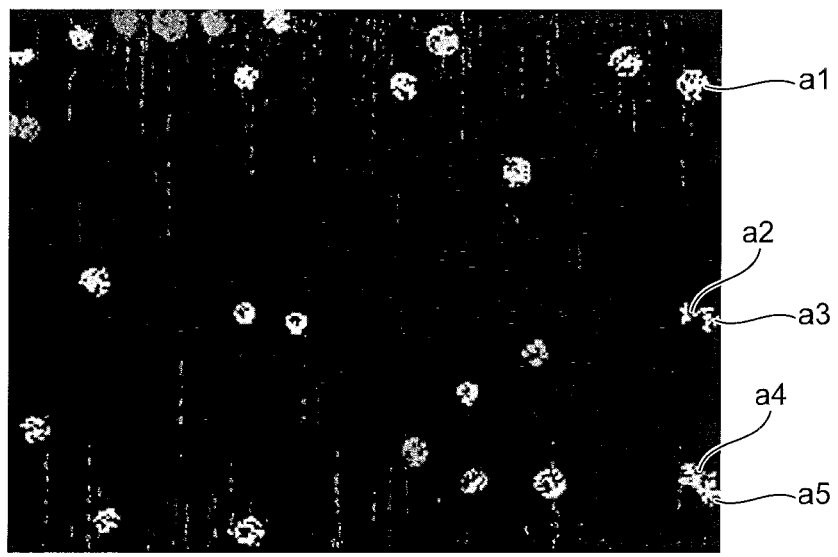
FIG. 4B shows an example of an extraction image of a nucleus area obtained by an analysis on the image shown in FIG. 4A.

FIG. 4B shows an image which is obtained by performing the analysis on the RGB image shown in FIG. 4A at step S102 and an extraction image in which a nucleus area stained with hematoxylin (dye H) is extracted. The extraction image is obtained by extracting a pixel having a pixel value included in a color range of the dye H.

Figures 4C, 4D:
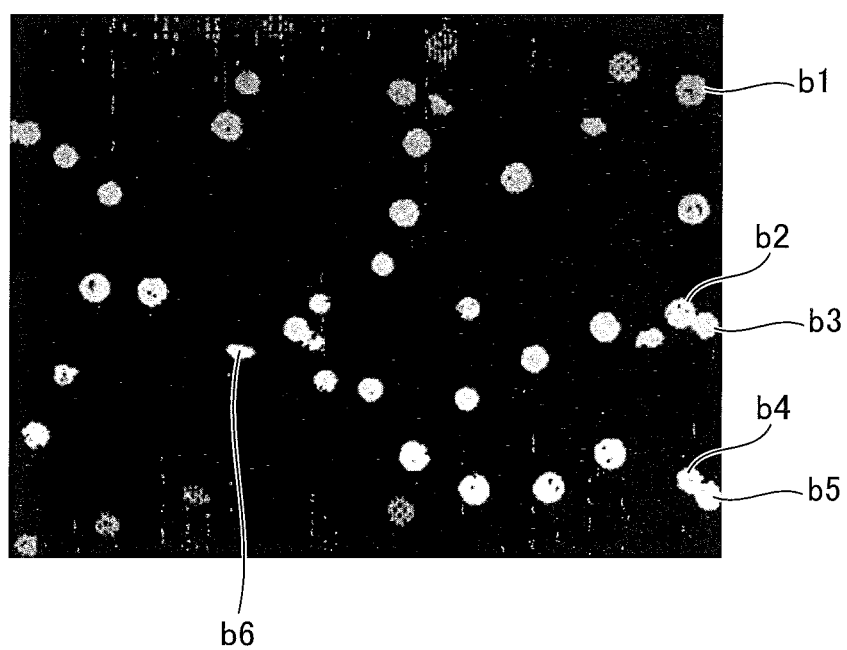
FIG. 4C is a table of a calculation example of analysis values of nucleus areas shown in FIGS. 4B.
FIG. 4D shows an example of nucleus areas extracted by using spectroscopic data obtained by a spectroscopic measurement.

FIG. 4C is a table of feature data (area, perimeter, and degree of circularity) calculated for nucleus areas a1, a2, ... shown in FIG. 4B. Here, an abnormality in the pathological specimen can be determined based on a degree of atypism of an extracted nucleus area. The atypism is feature data that shows a degree to which the extracted nucleus area is different in size or shape from a normal nucleus. Specifically, since a nucleus generally has almost circular shape, the atypism can be expressed by a degree of circularity (degree of circularity=$4\pi \times$area/perimeter$^2$) calculated by using an area and a perimeter of a nucleus area, for example. In this case, a smaller value for the atypism (degree of circularity) shows that the shape of a nucleus area as a determination target is more different from a circular shape, in other words, that a degree to which the nucleus area is different from a normal nucleus is larger. At step S103, a nucleus area whose atypism is smaller than a predetermined threshold value is determined to be an abnormal site and to be a target of the spectroscopic measurement.

For example, the degree of circularity of each of the nucleus areas a2 to a5 which have shapes significantly different from a circular shape among the nucleus areas a1, a2, ... shown in FIG. 4B has comparatively small value as shown in FIG. 4C. At steps S104 to S106, the spectroscopic measurement is performed on those nucleus areas a2 to a5.

FIG. 4D shows an extraction image of nucleus areas extracted by an analysis using the spectroscopic data at step S108. Nucleus areas b1, b2, ... shown in FIG. 4D correspond to nucleus areas a1, a2, ... shown in FIG. 4B. As is clear from the comparison with FIG. 4B, the nucleus areas a2 to a5 which are determined to be abnormal sites in the analysis only with the RGB image are determined to be normal nucleus areas b2 to b5 in the analysis using the spectroscopic data. In addition, a nucleus area corresponding to a nucleus area b6 shown in FIG. 4D is not shown in FIG. 4B. More specifically, a nucleus area which cannot be extracted in the RGB image analysis is extracted in the analysis using the spectroscopic data.

The reason why there arises a difference between the result of the RGB image analysis and the result of the analysis using the spectroscopic data is as follows.

Figure 5A:
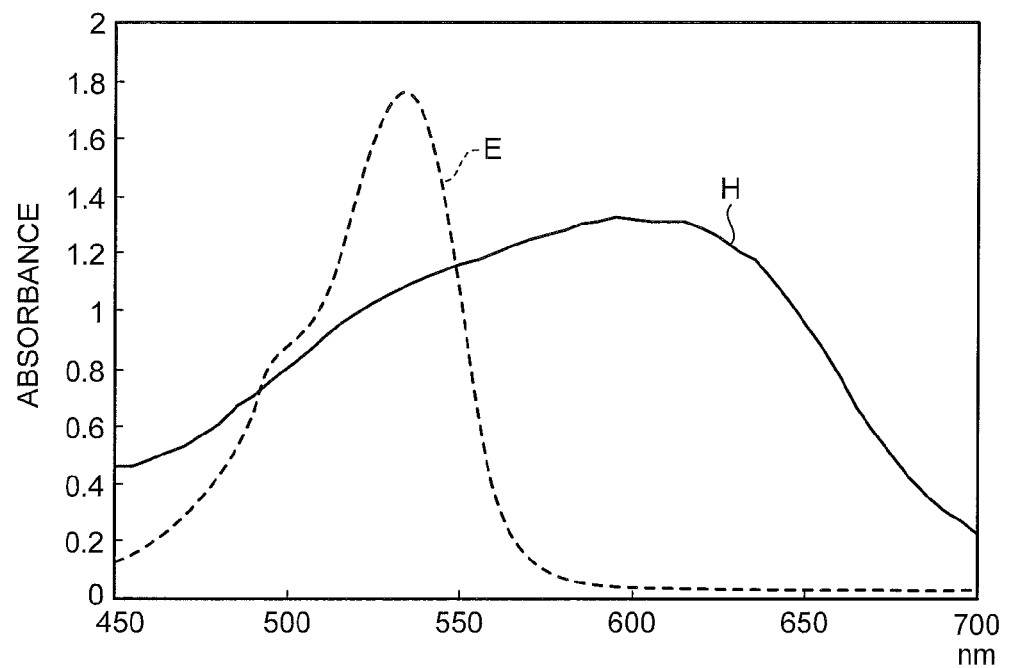
FIG. 5A shows an example of an absorbance spectrum of an HE-stained pathological specimen.
Figure 5B:
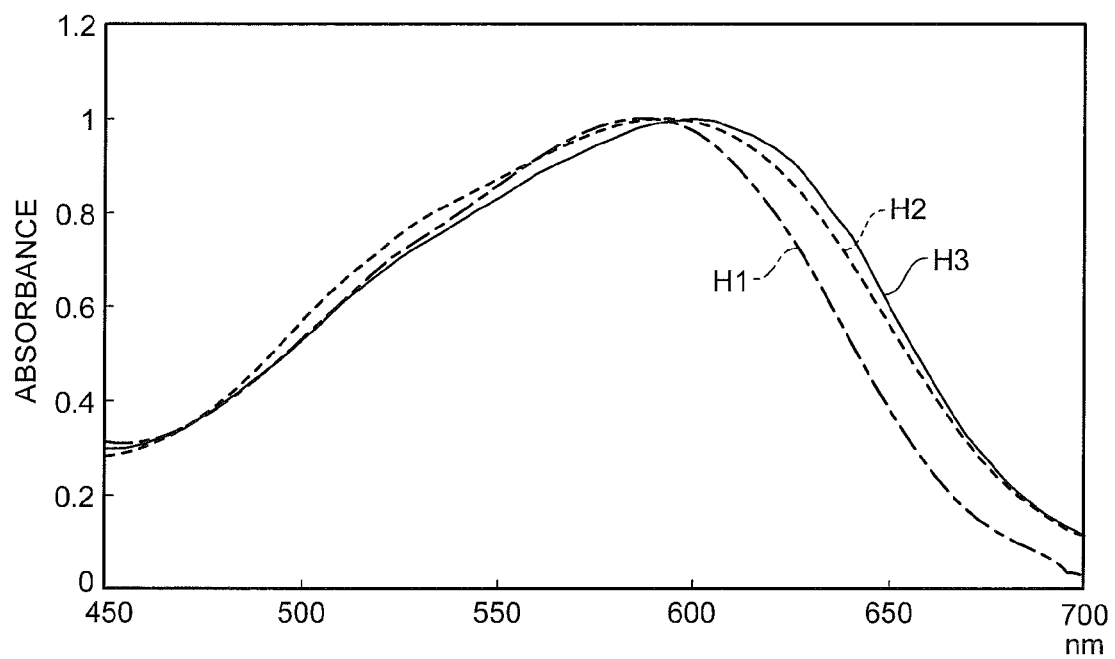
FIG. 5B shows an example of dispersion, arising depending on each specimen or in staining, in an absorbance spectrum of hematoxylin.

Dye components of the HE-stained pathological specimen are three, for example, hematoxylin (dye H) with which a cell nucleus is stained, eosin (dye E) with which a cell cytoplasm is stained, and else dye component {eosin with which a red blood cell is stained and a not-stained red blood cell color (dye R)}. FIG. 5A shows an example of an absorbance spectrum of the hematoxylin (H) and the eosin (E) of an HE-stained pathological specimen. FIG. 5B shows an example of dispersion, arising depending on each specimen or each staining facility, in an absorbance spectrum (H1, H2, and H3) of hematoxylin. When the dispersion in absorbance spectrum arises for each specimen in this manner, there is an influence on extraction accuracy of a nucleus area by the analysis only with an RGB image. In response to this, by performing a spectroscopic measurement in which absorption of a homochromatic light corresponding to a dye component is measured with respect to a nucleus area having a possibility that the shape is not extracted accurately due to the dispersion, it becomes possible to accurately extract a nucleus area.

Modified Example 1-1

Figure 6:
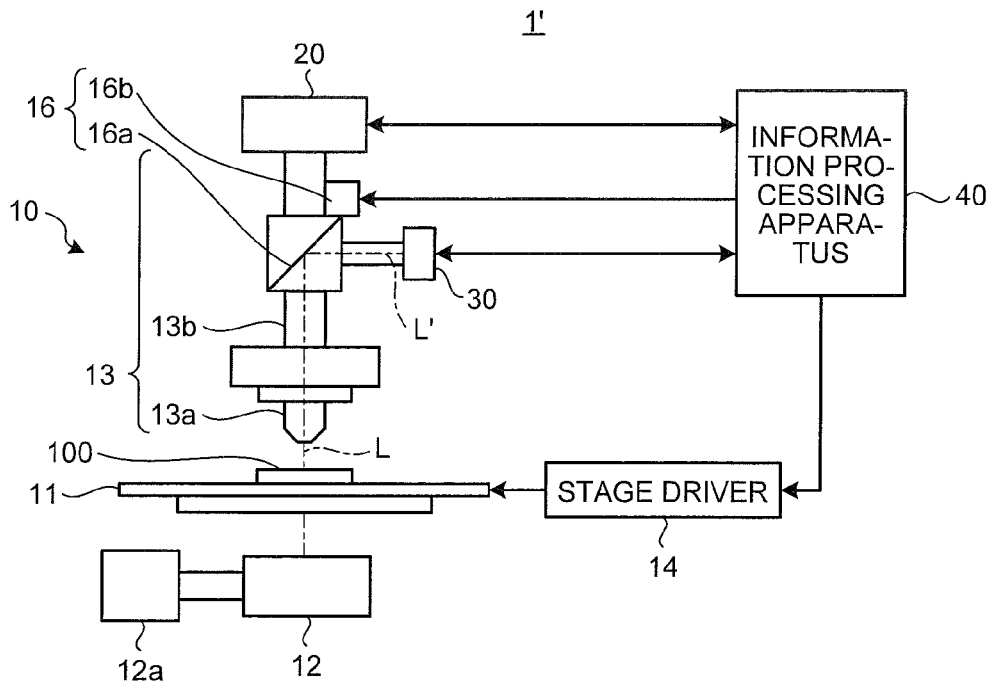
FIG. 6 schematically shows a configuration example of a microscope system according to a modified example 1-1.

Next, a modified example of the microscope system according to the first embodiment of the present invention will be explained. FIG. 6 schematically shows a configuration example of a microscope system according to a modified example 1-1. The modified example 1-1 is configured so that an optical path of the observation light from the specimen 100 is alternately switched to the direction of the RGB imaging device 20 and the direction of the spectroscopic measurement device 30.

Specifically, an optical path switching unit 16 is provided on an optical path of the lens barrel 13b in a microscope system 1'. The optical path switching unit 16 is provided with a total reflection mirror 16a provided in such a manner that it can be freely inserted and pulled out with respect to the optical path of the observation light coming through the objective lens 13a and a switching device 16b that causes the total reflection mirror 16a to be inserted to and pulled out from the observation optical axis L under the control of the control unit 410. The optical path switching unit 16 causes, in a state where the total reflection mirror 16a is pulled out from the observation optical axis L, the observation light to be transmitted linearly (total transmission state) and guided to the direction of the RGB imaging device 20, and causes, in a state where the total reflection mirror 16a is inserted on the observation optical axis L, all the observation light to be reflected (total reflection state) to be guided to the direction of the spectroscopic measurement device 30 (i.e., the direction along the optical axis L'). FIG. 6 shows the total reflection state.

In the case of using the optical path switching unit 16, the control unit 410 controls the switching device 16b to insert the total reflection mirror 16a on the observation optical axis L at a time when the spectroscopic measurement device 30 performs the spectroscopic measurement with respect to the specimen 100.

Modified Example 1-2

The analyzing process using spectroscopic data obtained by the spectroscopic measurement device 30 may be performed by a different apparatus from the information processing apparatus 40. Specifically, an information processing apparatus for spectroscopic data analyzing process is connected to the information processing apparatus 40 so that data can be transmitted and received and the information processing apparatus 40 outputs the spectroscopic data that the spectroscopic measurement controller 403 has received from the spectroscopic measurement device 30 directly to the information processing apparatus for spectroscopic data analyzing process. Or, the spectroscopic data that the spectroscopic measurement controller 403 has received from the spectroscopic measurement device 30 may be stored in a portable information recording medium and transferred to the other information processing apparatus via the information recording medium. Since the information processing apparatus 40 can dispense with the analyzing process on spectroscopic data generally with high load according to the modified example 1-2, it becomes possible to reduce the load and have an increase in speed of other processes (the analysis and the controlling process in the first analyzer 405).

Modified Example 1-3

The first embodiment can be applied not only to the process on one image obtained by imaging a specimen within a range of a field of view of the microscope device but also to a system in which a plurality of partial RGB images obtained by performing the imaging multiple times while shifting the range of the field of view of the microscope device with respect to the specimen are put together to generate one image. This system is known as virtual slide system.

In the virtual slide system, the RGB imaging is performed by the RGB imaging device 20 while the stage driver 14 shown in FIG. 1 moves the stage 11 by a predetermined measure from a predetermined base point in the XY plane under the control of the control unit 410 to sequentially shift an observation area of the specimen 100 within the field of view of the objective lens 13a. In this case, the spectroscopic measurement with respect to the abnormal site detected by the analysis on the RGB image may be performed after the RGB imaging with respect to all observation areas of the specimen 100 ends or each time when the RGB imaging with respect to one observation area ends.

Since the spectroscopic measurement is performed only with respect to a spectroscopic measurement position within an observation area in which an abnormal site is detected, it becomes possible according to the modified example 1-3 to obtain image information with high accuracy on a necessary area (abnormal site) while suppressing an increase in examination time in total with respect to the specimen 100.

Second Embodiment

Figure 7:
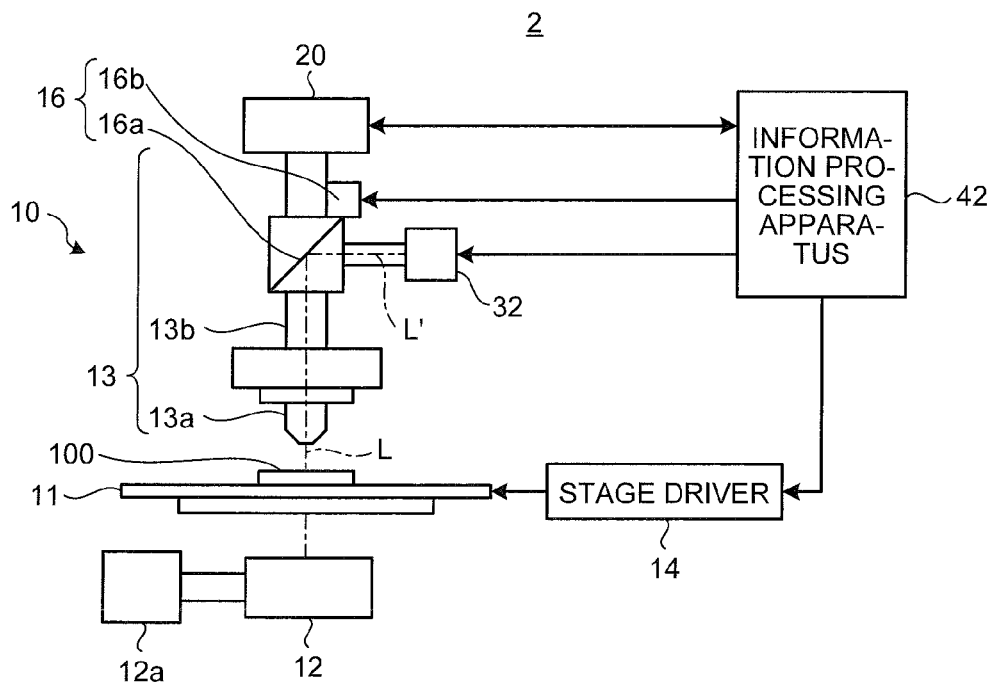
FIG. 7 schematically shows a configuration example of a microscope system according to a second embodiment of the present invention.

Next, a second embodiment of the present invention will be explained. FIG. 7 schematically shows a configuration example of a microscope system according to a second embodiment. As shown in FIG. 7, a microscope system 2 is provided with a multispectral (MS) imaging device 32, an information processing apparatus 42, and an optical path switching unit 16, instead of the spectroscopic measurement device 30, the information processing apparatus 40, and the beam splitter 15 shown in FIG. 1. Other components are the same as those shown in FIG. 1. The configuration and the operation of the optical path switching unit 16 are the same as those explained in the modified example 1-1.

The MS imaging device 32 is a multispectral camera that performs a multispectral imaging to obtain an observation image of the specimen 100 in a frame sequential method while switching among a plurality of bandpass filters whose wavelength bands of lights to be transmitted are different from each other. It is preferable that at least four bandpass filters are used. The MS imaging device 32 performs an MS imaging with respect to the specimen 100 within an image obtainment range which is the same field of view as the RGB imaging device 20, i.e., the field of view determined depending on the magnification of the objective lens 13a, and inputs image data of an MS image generated by the MS imaging (MS image data) to the information processing apparatus 42. A pixel value of each of pixels constituting the MS image corresponds to an intensity of an observation light in a band of each bandpass filter, i.e., spectroscopic data for each band at each corresponding point on the specimen 100.

Figure 8:
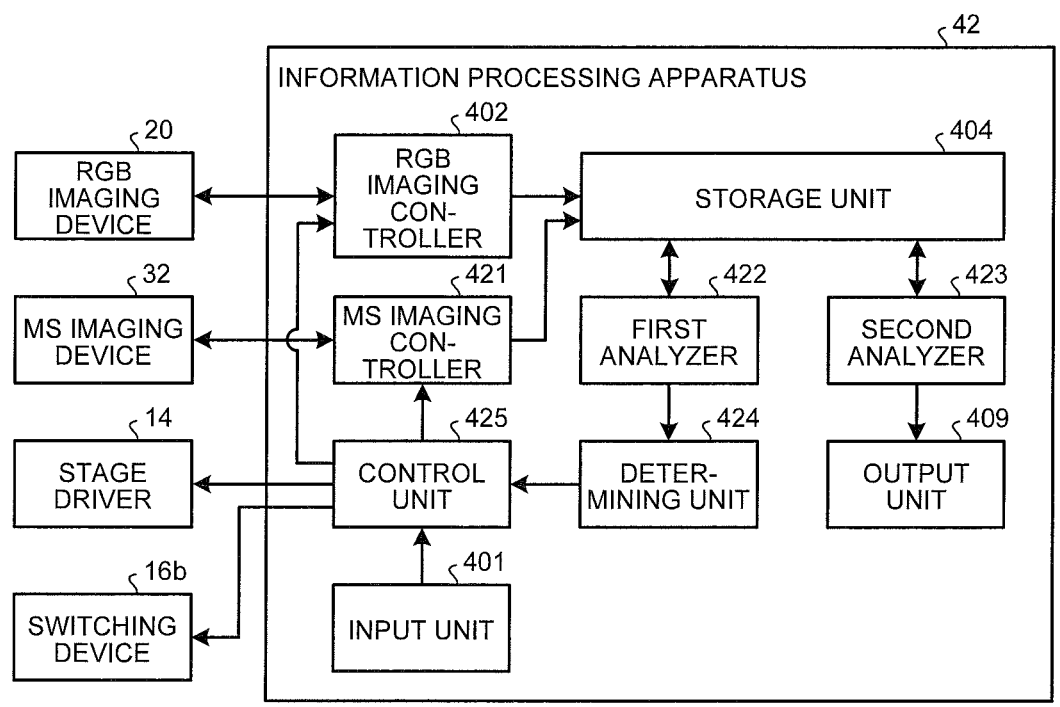
FIG. 8 is a block diagram of a configuration example of the information processing apparatus shown in FIG. 7.

FIG. 8 is a block diagram of a configuration example of the information processing apparatus 42 shown in FIG. 7. As shown in FIG. 8, the information processing apparatus 42 is provided with an input unit 401, an RGB imaging controller 402 that controls the operation of the RGB imaging device 20, an MS imaging controller 421 that controls the operation of the MS imaging device 32, a storage unit 404, a first analyzer 422 that analyzes the RGB image obtained in the RGB imaging device 20, a second analyzer 423 that analyzes the MS image obtained in the MS imaging device 32, a determining unit 424 that determines a necessity of obtaining spectroscopic information, an output unit 409, and a control unit 425 that controls these units. Among these units, the configuration and the operation of the input unit 401, the RGB imaging controller 402, the storage unit 404, and the output unit 409 are the same as those shown in FIG. 1.

The MS imaging controller 421 generates and transmits to the MS imaging device 32, a control signal that causes an execution of the MS imaging of the specimen 100, and accepts an input of and stores in the storage unit 404 MS image data generated in the MS imaging device 32.

The first analyzer 422 performs an analyzing process of extracting tissues appropriate to an examination purpose from an RGB image of the specimen 100 and calculating feature data of each of the extracted tissues, similarly to the first analyzer 405 shown in FIG. 2.

The second analyzer 423 performs an analyzing process of extracting a predetermined tissue from the MS image of the specimen 100 and calculating feature data and the like of the extracted tissue.

The determining unit 424 determines a necessity of performing the MS imaging of the specimen 100 and obtaining spectroscopic information based on the result of the analysis by the first analyzer 422.

The control unit 425 controls the units constituting the information processing apparatus 42 and controls, when the obtainment of spectroscopic information is determined to be necessary in the determining unit 424, the MS imaging controller 421, the stage driver 14, and the switching device 16b of the optical path switching unit 16 to perform the MS imaging on the same image obtainment range as the RGB image.

Figure 9:
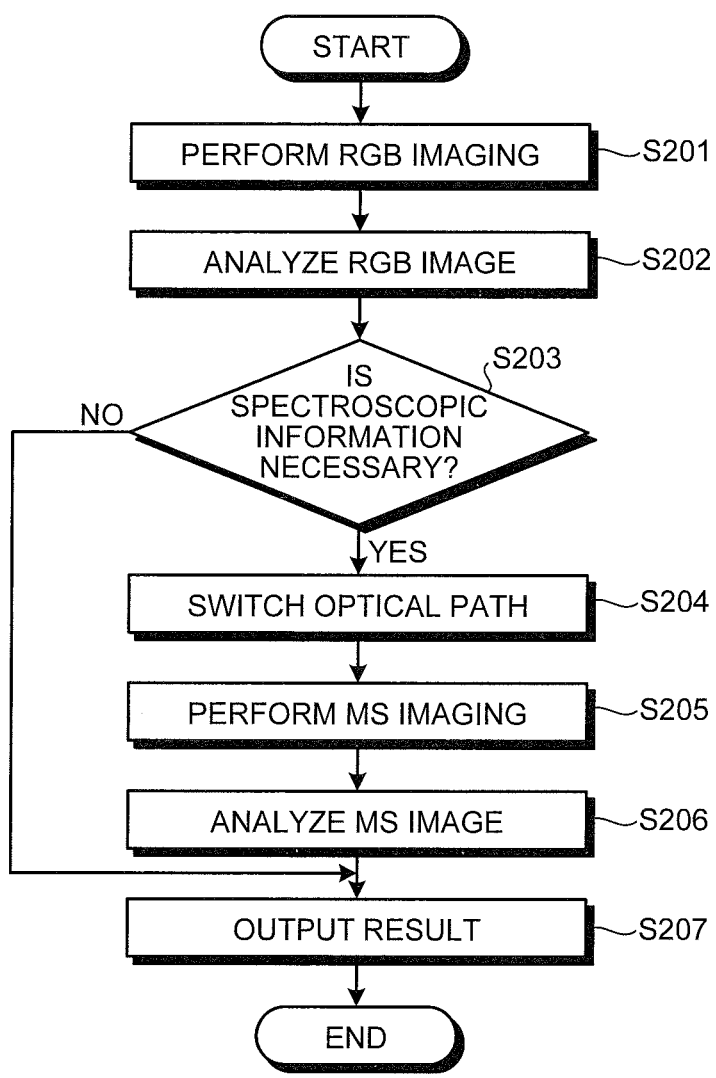
FIG. 9 is a flowchart of an operation of the microscope system shown in FIG. 7.

Next, an operation of the microscope system 2 will be explained. FIG. 9 is a flowchart of an operation of the microscope system 2.

First at step S201, the RGB imaging device 20 performs the RGB imaging with respect to the specimen 100 to obtain an observation image within an image obtainment range. On this occasion, the control unit 425 controls the switching device 16b to set the optical path of the observation light at a side of the optical axis L so that the observation light is made to enter the RGB imaging device 20.

At step S202, the first analyzer 422 performs an analysis on the RGB image captured at step S201. The analysis method here is the same as that explained in the first embodiment (step S102 in FIG. 3).

At step S203, the determining unit 424 determines a necessity of obtaining spectroscopic information of the specimen 100 based on the analysis result of the RGB image. Here, the determination method is the same as that explained in the first embodiment (step S103 in FIG. 3).

When the obtainment of spectroscopic information is determined to be necessary ("Yes" at step S203), the control unit 425 controls the optical path switching unit 16 to cause the optical path of the observation light to be switched to the direction along the optical axis L' so that the observation light is made to enter the MS imaging device 32 (step S204).

At step S205, the MS imaging device 32 performs the MS imaging with respect to the specimen 100 to obtain an observation image within the same image obtainment range as the RGB image captured at step S201 and generates MS image data.

At step S206, the second analyzer 423 performs an analysis on the MS image captured at step S205. The analysis method here adopts any of various known methods. For example, the second analyzer 423 obtains a pixel value of each of pixels constituting a spectral image in each band capturing the specimen 100 and estimates an amount of dye at a position corresponding to the pixel on the specimen 100. The second analyzer 423 reforms an image of the specimen 100 based on the estimated dye amount. Besides, the second analyzer 423 extracts predetermined tissues based on the reformed image and calculates feature data of each of the extracted tissues.

At step S207, the output unit 409 outputs and causes the display unit to display a result of the analysis (the reformed image, the feature data, and the like) by the second analyzer 423. Here, the contents to be output are the same as those at step S109 in FIG. 3.

On the other hand, when the obtainment of spectroscopic information is determined not to be necessary ("No" at step S203), the operation moves directly to step S207. In this case, the output unit 409 outputs the result of the analysis on the RGB image (step S207).

As explained above, whether or not the MS imaging is performed with respect to the specimen 100 is determined based on the analysis result of the RGB image in the second embodiment. Specifically, the MS imaging and the MS image analysis which realize high accuracy, however require long time for the processes are performed only when needed, so that an efficient examination can be performed while a necessary accuracy is kept.

Since spectroscopic data is obtained by the MS imaging, it is possible according to the second embodiment to obtain the spectroscopic data by performing the imaging whose number of times is just as many as the number of bands, irrespective of the number of abnormal sites included in one field of view. Thus, when the number of abnormal sites included in one field of view is large, it is possible to reduce the time required for the obtainment of spectroscopic data, compared to the spectroscopic measurement.

Moreover, since the number of specimens on which the MS imaging is performed is limited in examining a large number of specimens, it becomes possible according to the second embodiment to improve examination efficiency and throughput in total.

Modified Example 2-1

The second embodiment may be applied to the virtual slide system. In this case, it is preferable that the information processing apparatus 42 performs an analysis on an RGB image each time when the RGB imaging is performed with respect to one observation area of the specimen 100 and performs the MS imaging in the same field of view with respect to the observation area for which the obtainment of spectroscopic information is determined to be necessary. Since an MS image totally at the same position and in the same field of view as the RGB image can thus be obtained, it becomes possible to naturally join the RGB image of a given observation area and an image reformed based on the MS image of an adjacent observation area.

Modified Example 2-2

Figure 10:
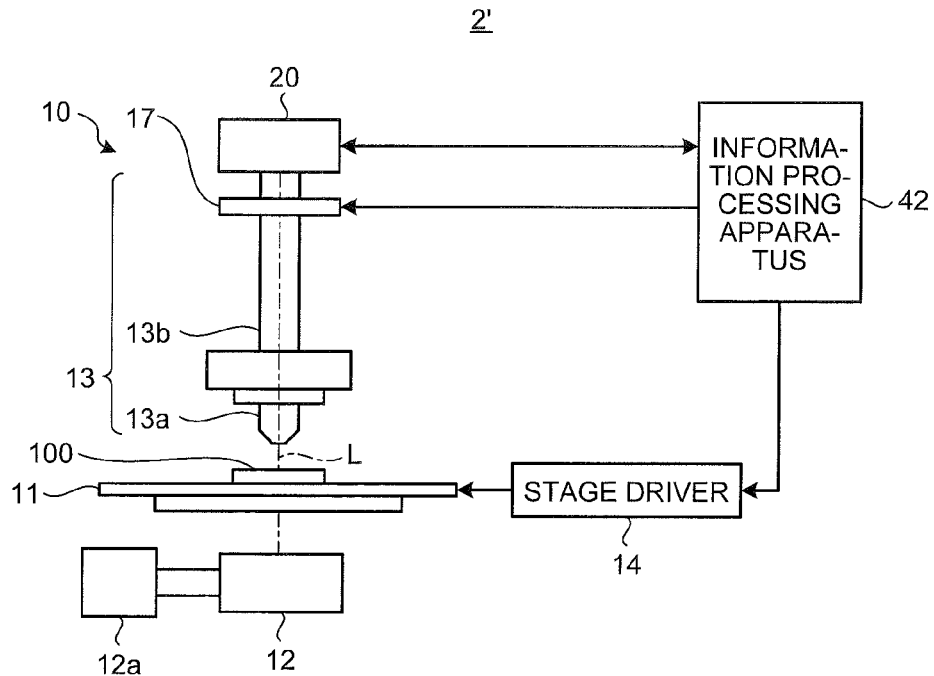
FIG. 10 schematically shows a configuration example of a microscope system according to a modified example 2-2.

FIG. 10 schematically shows a configuration example of a microscope system 2' according to a modified example 2-2 of the second embodiment. While the RGB imaging and the MS imaging are performed by respective imaging devices in the second embodiment, the both imagings can be performed by one imaging device. In this case, a filter switching unit 17 is provided in the lens barrel 13b and the RGB imaging device 20 is made to perform the RGB imaging and the MS imaging as shown in FIG. 10.

The filter switching unit 17 is provided with a plurality of (preferably at least four) bandpass filters whose wavelength bands of lights to be transmitted are different from each other and a switching device that switches an insertion state (insertion/non-insertion) to the observation optical axis L of these bandpass filters and switches the kind of bandpass filters when the bandpass filter is inserted to the observation optical axis L. The switching device operates under the control of the control unit 425.

In obtaining an RGB image in the microscope system 2', the information processing apparatus 42 controls the filter switching unit 17 to switch over to a non-insertion state of the bandpass filters and controls the RGB imaging device 20 to perform the imaging. In obtaining an MS image, the information processing apparatus 42 controls, after controlling the filter switching unit 17 to insert the bandpass filters to the observation optical axis L, the RGB imaging device 20 to perform the imaging while controlling the filter switching unit 17 to switch the kind of the bandpass filters.

According to the modified example 2-2, it becomes possible to reduce in size of and the cost for the microscope system.

Third Embodiment

Next, a third embodiment of the present invention will be explained. Though an entire configuration of a microscope system according to a third embodiment is the same as that of the microscope system 2 shown in FIG. 7, an information processing apparatus 43 shown in FIG. 11 is used instead of the information processing apparatus 42.

Figure 11:
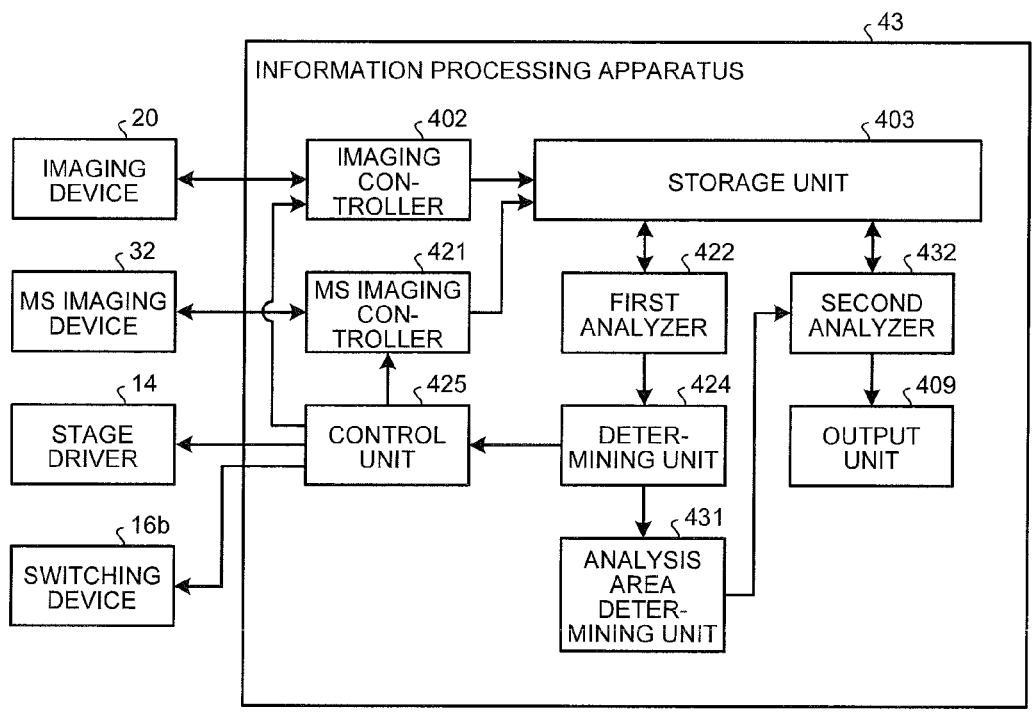
FIG. 11 is a block diagram of a configuration example of an information processing apparatus in a microscope system according to a third embodiment of the present invention.

As shown in FIG. 11, the information processing apparatus 43 is provided with an analysis area determining unit 431 and a second analyzer 432 instead of the second analyzer 423 shown in FIG. 8.

Based on the result of the analysis on the RGB image capturing the specimen 100, the analysis area determining unit 431 determines, when the obtainment of spectroscopic information is determined to be necessary by the information unit 424, an area (analysis area) on which an image analysis is performed in an MS image capturing the same image obtainment range. Specifically, an area, corresponding to an abnormal site detected from the RGB image, in the MS image is treated as an analysis area.

The second analyzer 432 performs an image analysis with respect to the analysis area determined by the analysis area determining unit 431.

Figure 12:
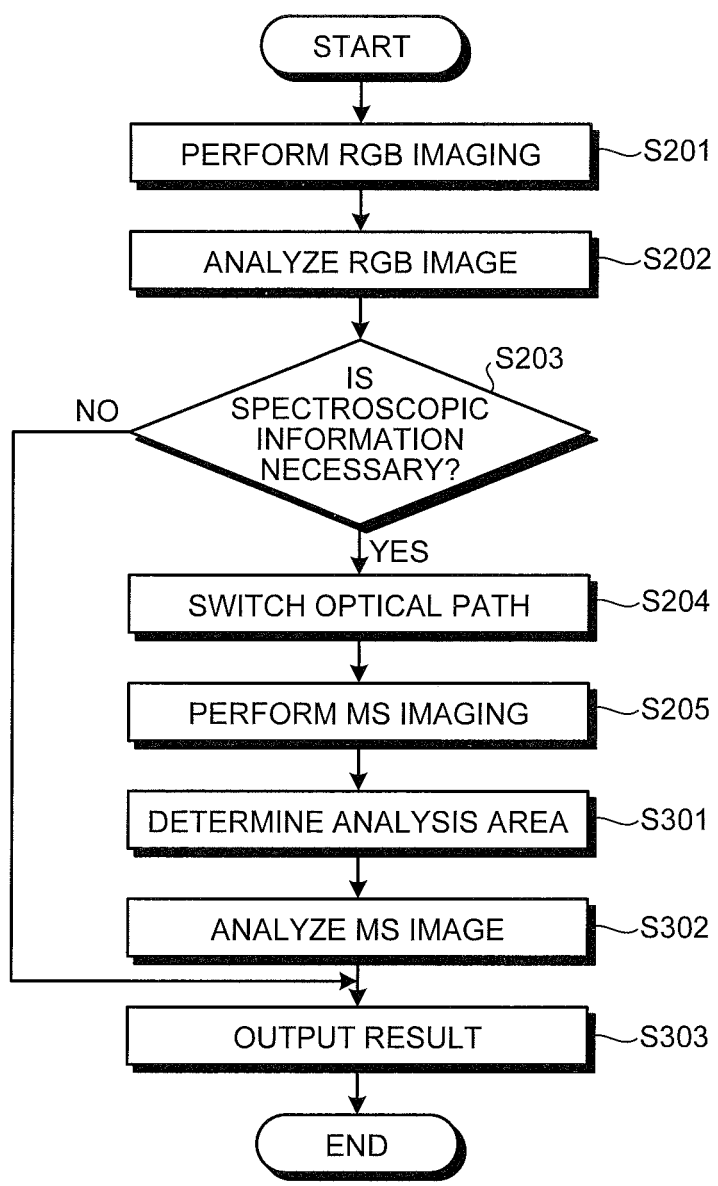
FIG. 12 is a flowchart of an operation of the microscope system according to the third embodiment of the present invention.

Next, an operation of the microscope system according to the third embodiment will be explained. FIG. 12 is a flowchart of an operation of the microscope system according to the third embodiment. Here, the operations at steps S201 to S205 in FIG. 12 are the same as those explained in the second embodiment.

At step S301 subsequent to step S205, the analysis area determining unit 431 determines an area of an abnormal site detected from the RGB image as an analysis area and outputs area information based on the analysis result of the RGB image capturing the specimen 100.

At step S302, the second analyzer 432 performs an image analysis with respect to an analysis area in the MS image based on the area information output from the analysis area determining unit 431. For the analysis method, various known methods may be used. For example, the second analyzer 432 obtains a pixel value of each of pixels included in the analysis area from a spectral image in each band capturing the specimen 100 and estimates an amount of dye in an area corresponding to the pixel on the specimen 100. The second analyzer 432 reforms an image in the analysis area and calculates feature data of the reformed part based on the estimated dye amount. The second analyzer 432 may generate a composite image obtained by combining the image of the analysis area reformed from the MS image with the original RGB image and perform an image analysis on the composite image.

At step S303, the output unit 409 outputs a result of the analysis (the reformed image of the analysis area, the feature data, and the like) by the second analyzer 432. When the second analyzer 432 generates a composite image, the output unit 409 may output the composite image and a result of the analysis of the composite image.

When the obtainment of spectroscopic information is determined not to be necessary ("No" at step S203), the output unit 409 outputs only the analysis result of the RGB image (step S303).

As explained so far, whether or not the MS imaging is performed is determined based on the analysis result of the RGB image and the image analysis is performed only on the area, corresponding to the abnormal site detected by the analysis on the RGB image, in the MS image when the MS imaging is performed in the third embodiment. Thus, it becomes possible to obtain an analysis result with high accuracy with respect to a necessary area while reducing time required for the image analysis.

The third embodiment may be applied to the virtual slide system in which a plurality of images obtained by performing the imaging multiple times while shifting the range of the field of view of the microscope device with respect to the specimen are put together to generate one image.

Fourth Embodiment

Figure 13:
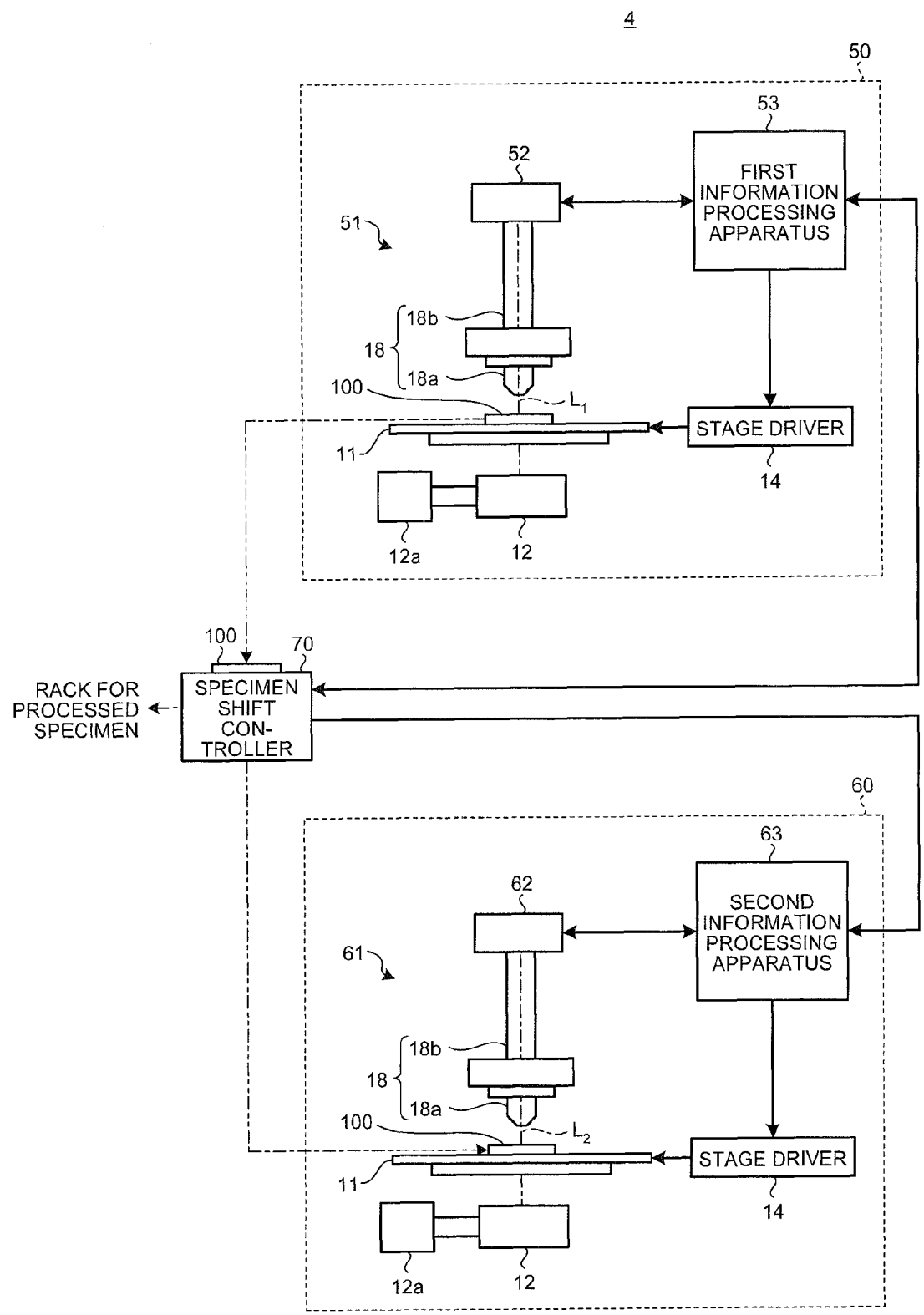
FIG. 13 schematically shows a configuration example of a microscope system according to a fourth embodiment of the present invention.

Next, a fourth embodiment will be explained. FIG. 13 schematically shows a configuration example of a microscope system according to a fourth embodiment. A microscope system 4 shown in FIG. 13 is provided with a first microscope system 50, a second microscope system 60, and a specimen shift controller 70.

The first microscope system 50 is provided with a first microscope 51, an RGB imaging device 52, and a first information processing apparatus 53. The microscope 51 is provided with the stage 11 on which the specimen 100 is placed, the illumination optical system 12 that transmits an illumination from a rear surface side of the specimen 100, an observation optical system 18 that makes the illumination light transmitted through the specimen 100 incident, and the stage driver 14 that adjusts the position of the stage 11. The observation optical system 18 includes an objective lens 18a and a lens barrel 18b that guides an observation light transmitted through the objective lens 18a to the RGB imaging device 52 along an observation optical axis $L_1$. The RGB imaging device 52 is an RGB camera provided with an imaging element such as a CCD and arranged at an end part of the lens barrel 18b so that a center of an RGB image to be obtained locates on the observation optical axis L.

The second microscope system 60 is provided with a second microscope 61 having the same configuration as the first microscope 51, a spectroscopic measurement device 62, and a second information processing apparatus 63. The spectroscopic measurement device 62 is arranged at an end part of the lens barrel 18b so that a measurement center locates on an observation optical axis $L_2$.

The specimen shift controller 70 shifts the specimen 100 between the first microscope system 50 and the second microscope system 60 and in their anteroposterior conveyance path.

Figure 14:
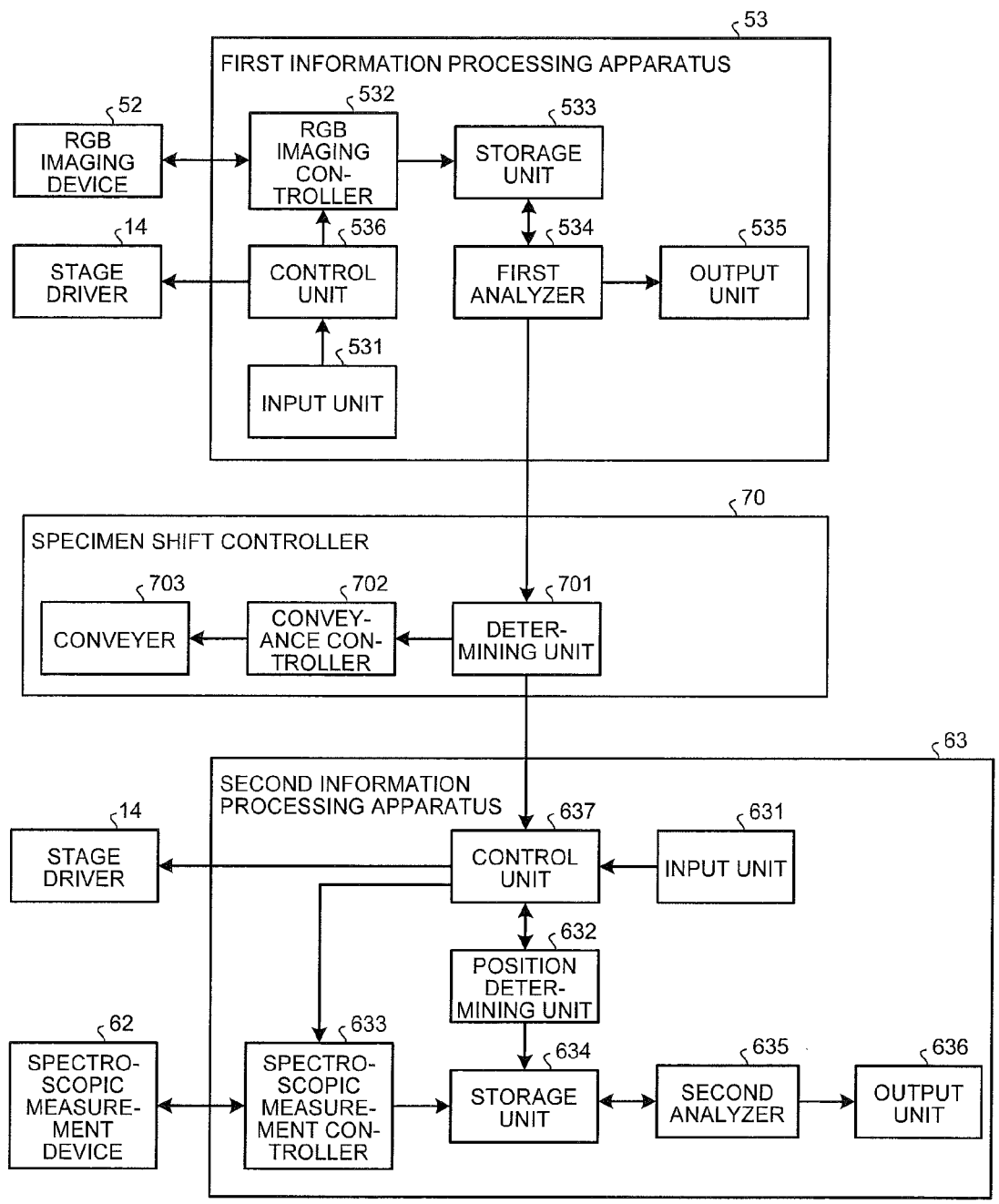
FIG. 14 is block diagram of a configuration example of the microscope system shown in FIG. 13.

FIG. 14 is block diagram of a configuration example of the microscope system 4.

The first information processing apparatus 53 is provided with an input unit 531 that accepts an input of information concerning a process in the information processing apparatus 53; an RGB imaging controller 532 that controls an operation of the RGB imaging device 52; a storage unit 533; a first analyzer 534 that analyzes RGB image data obtained in the RGB imaging device 52; an output unit 535 that causes a display device to display information including a process status, a process result, and the like in the information processing apparatus 53; and a control unit 536 that controls these units overall and the operation of the stage driver 14.

The specimen shift controller 70 is provided with a determining unit 701 that is connected to the first information processing apparatus 53 and the second information processing apparatus 63 in a such manner that data can be transmitted and received, and determines a necessity of obtaining spectroscopic information in addition with respect to the specimen 100 based on the analysis result on the RGB image output from the first information processing apparatus 53; a conveyance controller 702 that determines a conveyance destination of the specimen 100 according to a result of the determination by the determining unit 701; and a conveyer 703 that conveys the specimen 100 under the control of the conveyance controller 702.

The second information processing apparatus 63 is provided with an input unit 631 that accepts an input of information concerning a process of the information processing apparatus 63; a position determining unit 632 that determines a position at which spectroscopic measurement is performed on the specimen 100; a spectroscopic measurement controller 633 that controls an operation of the spectroscopic measurement device 62; a storage unit 634; a second analyzer 635 that analyzes spectroscopic data obtained in the spectroscopic measurement device 62; an output unit 636 that causes a display device to display information including a process status, a process result, and the like in the second information processing apparatus 63; and a control unit 637 that controls the operation of the stage driver 14 of the second microscope 61.

Figure 15:
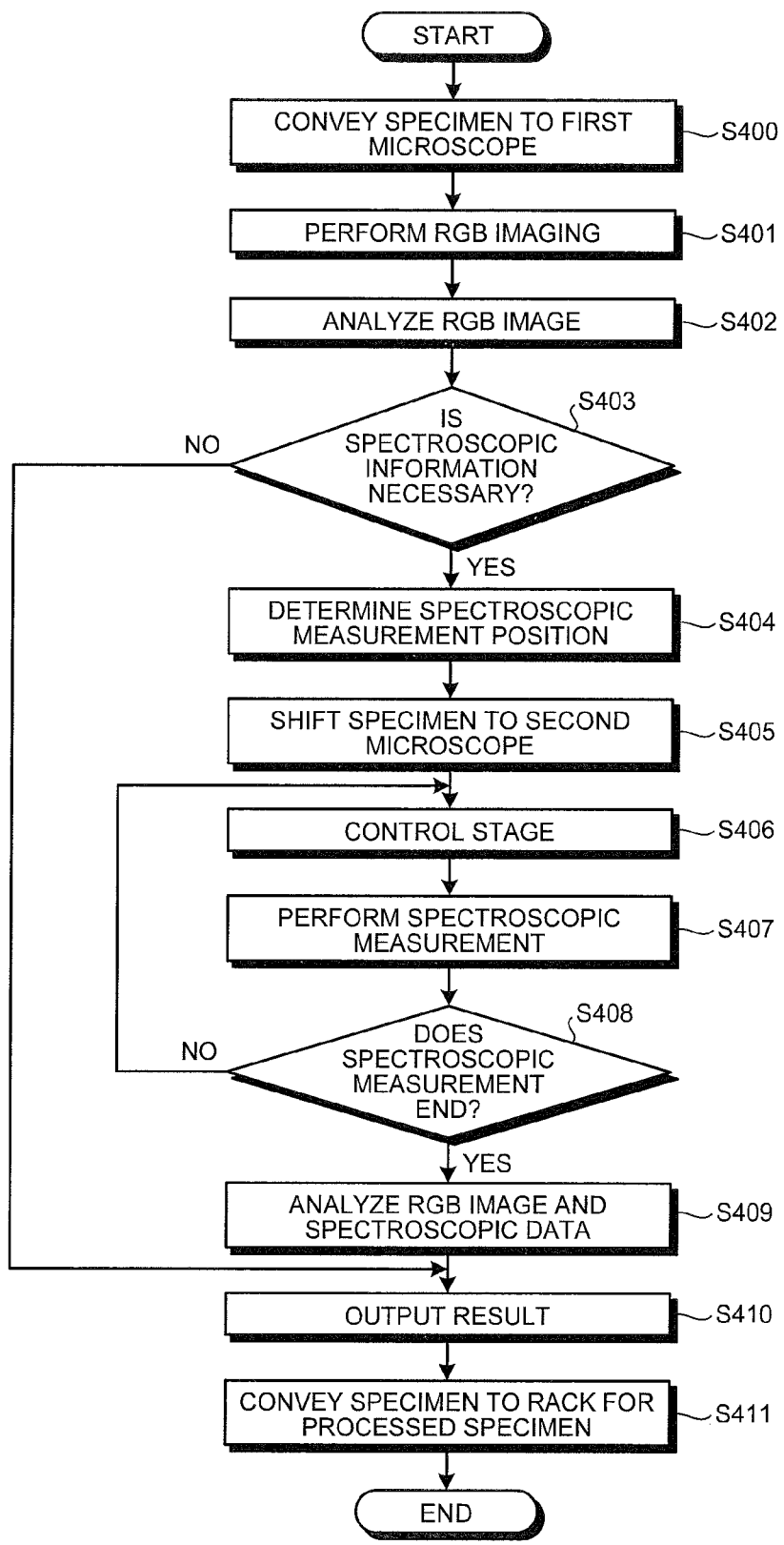
FIG. 15 is a flowchart of an operation of the microscope system shown in FIG. 13.

Next, an operation of the microscope system 4 will be explained. FIG. 15 is flowchart of an operation of the microscope system 4.

First at step S400, the specimen shift controller 70 conveys the specimen 100 from a not shown rack for unprocessed specimen to the stage 11 of the first microscope 51.

At step S401, the RGB imaging device 52 performs an RGB imaging with respect to the specimen 100 to obtain an observation image within an image obtainment range and generates RGB image data. The generated RGB image data is stored in the storage unit 533.

At subsequent step S402, the first analyzer 534 analyzes the RGB image captured at step S401 and transmits a result of the analysis (feature data and the like of extracted tissues) to the specimen shift controller 70.

At step S403, the determining unit 701 determines a necessity of obtaining spectroscopic information of the specimen 100 based on the analysis result of the RGB image. Here, the determination method is the same as step S103 in the first embodiment.

When the obtainment of spectroscopic information is determined to be necessary ("Yes" at step S403), the position determining unit 632 receives information including the determination result, the RGB image data, and the analysis result from the determining unit 701 and determines, as a spectroscopic measurement position, a position of each abnormal site detected from the specimen 100 based on the information (step S404).

At subsequent step S405, the conveyer 703 conveys the specimen 100 to the stage 11 of the second microscope 61 in accordance with the control of the conveyance controller 702.

At step S406, the control unit 637 controls the stage driver 14 to adjust the position of the stage 11 so that the spectroscopic measurement position determined by the position determining unit 632 is arranged at a center of the range of the measurement by the spectroscopic measurement device 62.

At step S407, the spectroscopic measurement device 62 performs the spectroscopic measurement with respect to each spectroscopic measurement position on the specimen 100 to generate spectroscopic data.

At step S408, the control unit 637 determines whether or not the spectroscopic measurement is performed with respect to all spectroscopic measurement positions. When there remains a position which needs the spectroscopic measurement ("No" at step S408), the operation returns to step S406. On the other hand, when the spectroscopic measurement is performed with respect to all the spectroscopic measurement positions ("Yes" at step S408), the operation moves to step S409.

At step S409, the second analyzer 635 performs an image analysis based on the spectroscopic data obtained by the spectroscopic measurement and the RGB image data received from the first information processing apparatus 53 by way of the specimen shift controller 70. Here, the analysis method is the same as that explained (at step S108 in FIG. 3) in the first embodiment.

At step S410, the output unit 636 outputs the analysis result by the second analyzer 635 to a display device and causes the display device to make a display.

Then at step S411, the specimen shift controller 70 conveys the specimen 100 from the stage 11 of the second microscope 61 to a rack for processed specimen.

When the obtainment of spectroscopic information is determined not to be necessary at step S403 ("No" at step S403), the output unit 535 outputs the result of the analysis, by the first analyzer 534, on the RGB image (step S410). In this case, the specimen shift controller 70 conveys the specimen 100 from the stage 11 of the first microscope 51 directly to the rack for processed specimen (step S411).

As explained above, since a specimen for which the obtainment of spectroscopic information is determined to be necessary as a result of the analysis on the RGB image in the first microscope system is shifted to the second microscope system to perform the spectroscopic measurement thereon, it is possible according to the fourth embodiment to perform the RGB imaging and the spectroscopic measurement in parallel. Thus, it becomes possible to reduce waiting time of a specimen on which only the process for the analysis on an RGB image will do in screening and the like in which a large number of specimens are processed and to improve throughput.

Fifth Embodiment

Figure 16:
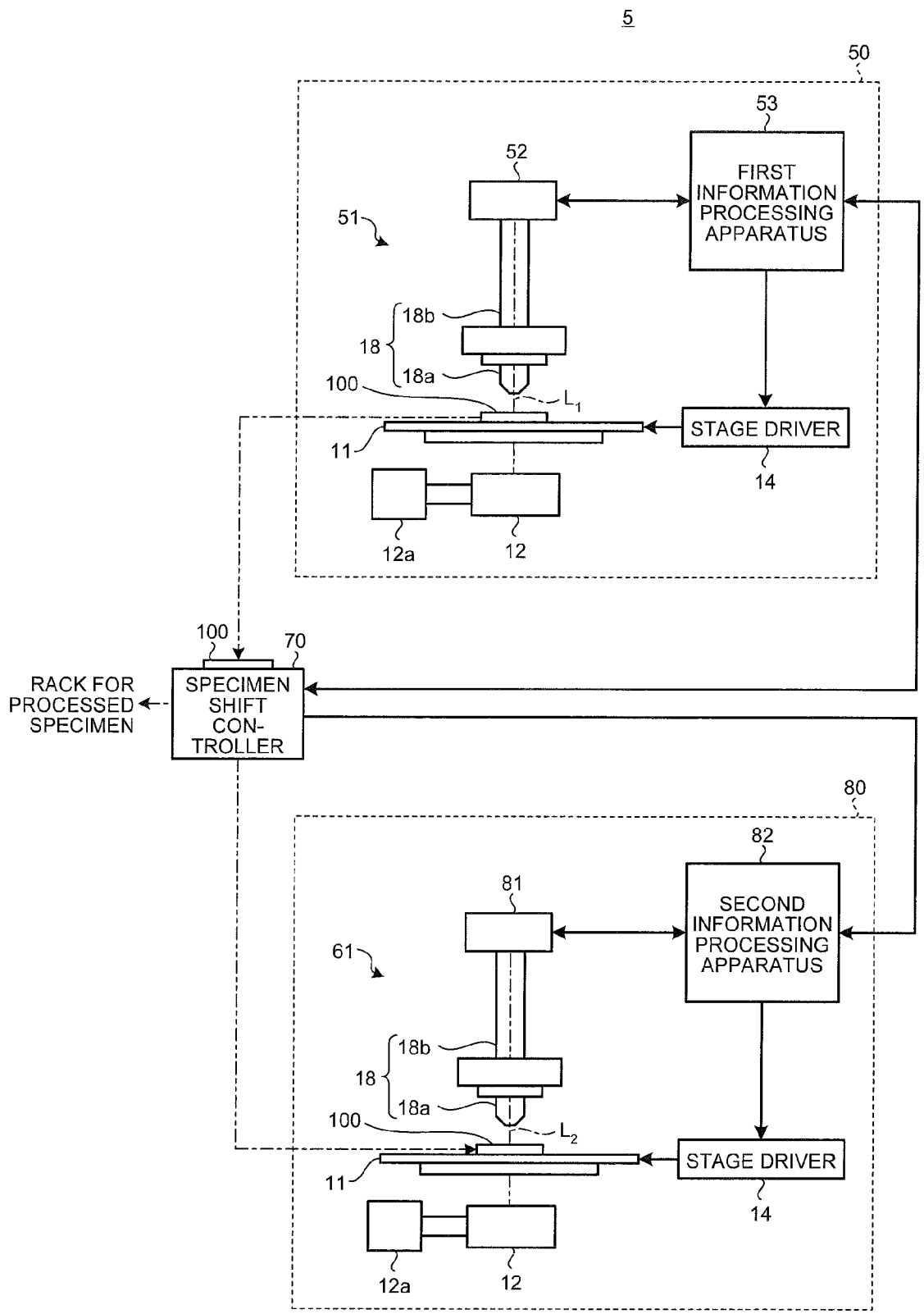
FIG. 16 schematically shows a configuration example of a microscope system according to a fifth embodiment of the present invention.

Next, a fifth embodiment will be explained. FIG. 16 schematically shows a configuration example of a microscope system according to a fifth embodiment. As shown in FIG. 16, a microscope system 5 is provided with a second microscope system 80 instead of the second microscope system 60 shown in FIG. 14. Other components are the same as the fourth embodiment.

The second microscope system 80 is provided with a second microscope 61, an MS imaging device 81, and a second information processing apparatus 82. The configuration of the second microscope 61 is the same as that explained in the fourth embodiment.

The MS imaging device 81 is a multispectral camera that performs a multispectral imaging to obtain an observation image of the specimen 100 in a frame sequential method while switching among a plurality of (at least four, for example) bandpass filters whose wavelength bands of lights to be transmitted are different from each other, and arranged at an end part of the lens barrel 18b so that a center of an MS image to be obtained locates on the observation optical axis L2.

Figure 17:
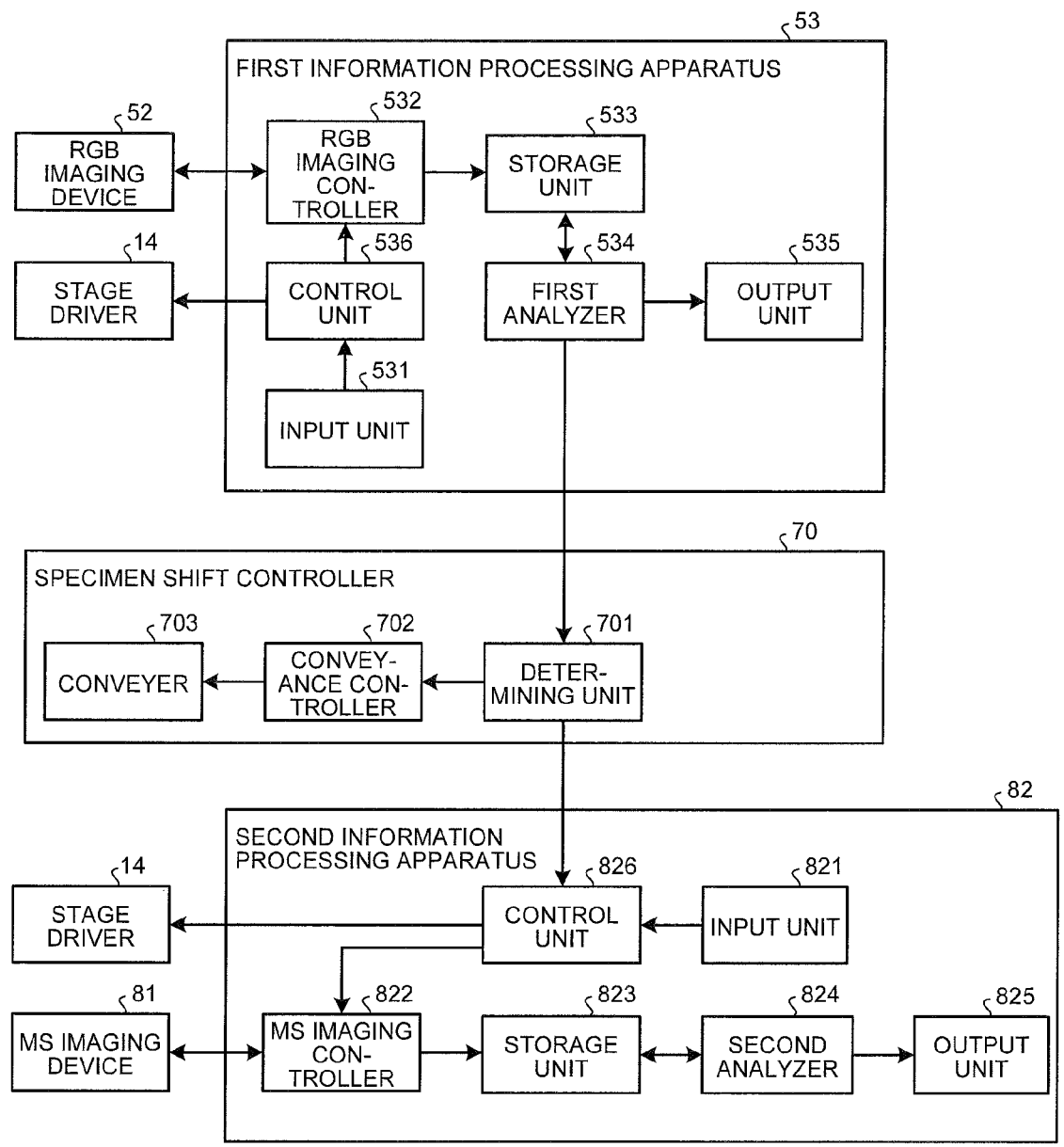
FIG. 17 is a block diagram of a configuration example of the microscope system shown in FIG. 16.

FIG. 17 is a block diagram of a configuration example of the microscope system 5. The configuration of the first information processing apparatus 53 and the configuration of the specimen shift controller 70 are the same as those explained in the fourth embodiment.

The second information processing apparatus 82 is provided with an input unit 821 that accepts an input of information concerning a process in the second information processing apparatus 82, an MS imaging controller 822 that controls the operation of the MS imaging device 81, a storage unit 823, a second analyzer 824 that analyzes the MS image obtained in the MS imaging device 81, an output unit 825 that causes a display device to display information including a process status, a process result, and the like in the second information processing apparatus 82, and a control unit 826 that controls these units overall and controls the operation of the stage driver 14 of the second microscope 61.

Figure 18:
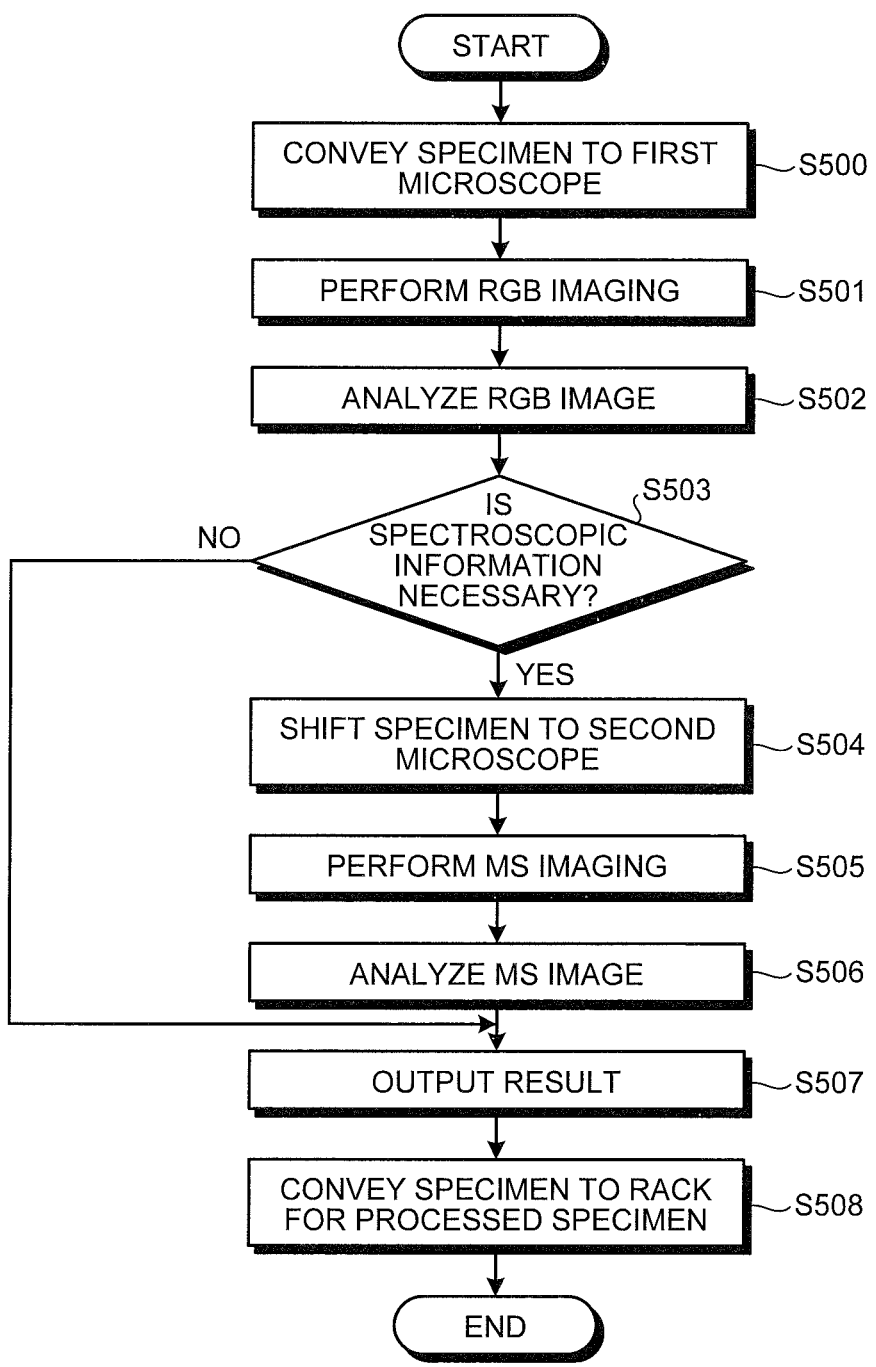
FIG. 18 is a flowchart of an operation of the microscope system shown in FIG. 16.

Next, an operation of the microscope system 5 will be explained. FIG. 18 is a flowchart of an operation of the microscope system 5. Steps S500 to S503 in FIG. 18 correspond to steps S400 to S403 in FIG. 15.

When the obtainment of spectroscopic information is determined to be necessary at step S503 ("Yes" at step S503), the specimen shift controller 70 conveys the specimen 100 to the stage 11 of the second microscope 61 (step S504).

At subsequent step S505, the control unit 826 controls the MS imaging controller 822 and the stage driver 14 to cause an execution of the MS imaging with respect to the specimen 100 to obtain an observation image within the same image obtainment range as the RGB image captured at step S501.

At step S506, the second analyzer 824 performs an analysis on the MS image captured at step S505. The analysis method here is the same as that explained (at step S206 in FIG. 9) in the second embodiment.

At step S507, the output unit 825 outputs the result, by the second analyzer 824, of the analysis on the MS image.

At step S508, the specimen shift controller 70 conveys the specimen 100 from the stage 11 of the second microscope 61 directly to the rack for processed specimen.

When the obtainment of spectroscopic information is determined not to be necessary at step S503 ("No" at step S503), the output unit 535 outputs the result of the analysis, by the first analyzer 534, on the RGB image (step S507). In this case, the specimen shift controller 70 conveys the specimen 100 from the stage 11 of the first microscope 51 directly to the rack for processed specimen (step S508).

As explained so far, since a specimen for which the obtainment of spectroscopic information is determined to be necessary as a result of the analysis on the RGB image in the first microscope system 50 is shifted to the second microscope system 80 to perform the MS imaging thereon, it is possible to perform the RGB imaging and the MS imaging in parallel. Thus, it becomes possible to reduce waiting time of a specimen on which only the process for the analysis of an RGB image will do in screening and the like in which a large number of specimens are processed and to improve throughput.

Modified Example 5-1

The second analyzer 824 may perform the analysis on an MS image only with respect to an area corresponding to an abnormal site detected from an RGB image, similarly to the third embodiment. In this case, it is only necessary that the second information processing apparatus 82 is further provided with an analysis area determining unit that determines an area on which an analysis is performed in the MS image based on the result of the analysis on the RGB image.

According to the present invention, it is possible to efficiently perform an image analysis with high accuracy since spectroscopic information is obtained only for a specimen whose detailed image information is needed based on a result of an analysis on an RGB image capturing a specimen.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A microscope system, comprising:
a first microscope that generates an observation image of a specimen;
an image obtaining unit that obtains an RGB image of the specimen;
a spectroscopic information obtaining unit that obtains spectroscopic information of the specimen;
a first analyzer that analyzes the RGB image to calculate feature data of the specimen;
a determining unit that:
compares the feature data of the specimen calculated by the first analyzer with a threshold value to detect one or more abnormal sites in the observation image of the specimen; and
determines that it is necessary to obtain the spectroscopic information in response to detecting one or more abnormal sites in the observation image of the specimen; and
a control unit that controls the spectroscopic information obtaining unit to obtain the spectroscopic information in response to the determining unit determining that it is necessary to obtain the spectroscopic information.

2. The microscope system according to claim 1, further comprising:
a position determining unit that determines a spectroscopic measurement position at which spectroscopic information of the specimen is obtained based on the feature data of the specimen calculated by the first analyzer,
wherein:
the spectroscopic information obtaining unit is a spectroscopic measurement device, and
the control unit controls an operation of the spectroscopic measurement device and a position of the specimen in the first microscope to obtain spectroscopic information at the spectroscopic measurement position.

3. The microscope system according to claim 2, further comprising:

a second analyzer that analyzes the specimen by using image information of the RGB image and the spectroscopic information concerning the spectroscopic measurement position.

4. The microscope system according to claim 1, wherein the spectroscopic information obtaining unit is a multiband imaging device having at least four bands.

5. The microscope system according to claim 4, further comprising:
a second analyzer that analyzes the specimen by using image information of a multiband image captured by the multiband imaging device.

6. The microscope system according to claim 4, further comprising:
an analysis area determining unit that determines an area which is used for an analysis in the multiband image captured by the multiband imaging device based on the feature data of the specimen calculated by the first analysis; and
a second analyzer that analyzes the specimen by using image information of the RGB image and image information of the multiband image concerning the area.

7. The microscope system according to claim 1, further comprising:
a splitter that causes an optical path of an observation light, generated in the first microscope, of the specimen to branch off to a direction of the image obtaining unit and a direction of the spectroscopic information obtaining unit, the image obtaining unit and the spectroscopic information obtaining unit being arranged at positions different from each other.

8. The microscope system according to claim 1, further comprising:
a switching unit that causes an optical path of an observation light, generated in the first microscope, for observing the specimen to be switched to one of a direction of the image obtaining unit and a direction of the spectroscopic information obtaining unit, the image obtaining unit and the spectroscopic information obtaining unit being arranged at positions different from each other.

9. The microscope system according to claim 1,
wherein the image obtaining unit is arranged to the first microscope,
wherein the microscope system further comprises:
a second microscope to which the spectroscopic information obtaining unit is arranged;
a conveyer that conveys the specimen from the first microscope to the second microscope; and
a conveyance controller that controls the conveyer in response to the determining unit determining that it is necessary to obtain the spectroscopic information.

10. The microscope system according to claim 1, further comprising:
a specimen position controller that controls a position of the specimen in the first microscope and causes the image obtaining unit to perform imaging multiple times and obtain partial RGB images of the specimen; and
an image processor that puts together the partial RGB images of the specimen obtained by performing the imaging multiple times.

11. The microscope system according to claim 1, wherein the feature data of the specimen comprises at least one of:
an area of a tissue in the observation image of the specimen;
a perimeter of the tissue;
a degree of circularity of the tissue; and
an atypism of the tissue calculated from the perimeter and the degree of circularity.

12. The microscope system according to claim 1,
wherein the feature data of the specimen in a degree of circularity calculated by using an area and a perimeter of a nucleus area in the observation image of the specimen, and
wherein the determining unit:
determines whether the degree of circularity is smaller than the threshold value;
detects the one or more abnormal sites in the observation image based on a determination that the degree of circularity is smaller than the threshold value; and
determines that it is necessary to obtain the spectroscopic information in response to detecting the one or more abnormal sites in the observation image of the specimen.

13. An information processing apparatus for controlling a microscope system comprising:
a microscope that generates an observation image of a specimen;
an image obtaining unit that obtains an RGB image of the specimen; and
a spectroscopic information obtaining unit that obtains spectroscopic information of the specimen, wherein the information processing apparatus comprises:
an analyzer that analyzes the RGB image to calculate feature data of the specimen;
a determining unit that:
compares the feature data of the specimen calculated by the analyzer with a threshold value to detect one or more abnormal sites in the observation image of the specimen;
determines that it is necessary to obtain the spectroscopic information in response to detecting one or more abnormal sites in the observation image of the specimen; and
a control unit that controls the spectroscopic information obtaining unit to obtain the spectroscopic information in response to the determining unit determining that it is necessary to obtain the spectroscopic information.

14. A non-transitory computer readable recording medium with an executable information processing program stored thereon for controlling a microscope system comprising:
a microscope that generates an observation image of a specimen;
an image obtaining unit that obtains an RGB image of the specimen; and
a spectroscopic information obtaining unit that obtains spectroscopic information of the specimen, wherein the program causes a computer to execute:
analyzing the RGB image to calculate feature data of the specimen;
comparing the feature data of the specimen with a threshold value to detect one or more abnormal sites in the observation image of the specimen;
determining that it is necessary to obtain the spectroscopic information in response to detecting one or more abnormal sites in the observation image of the specimen; and
controlling the spectroscopic information obtaining unit to obtain the spectroscopic information in response to determining that it is necessary to obtain the spectroscopic information.

* * * * *